(12) United States Patent
Einav et al.

(10) Patent No.: US 9,460,266 B2
(45) Date of Patent: Oct. 4, 2016

(54) SYSTEM AND A METHOD FOR SCORING FUNCTIONAL ABILITIES OF A PATIENT

(75) Inventors: Omer Einav, Emek Hefer (IL); Dikla Geva, Tel-Aviv (IL); Marina Kerzhner, Nazareth Ilit (IL); Doron Yoely, Hadera (IL)

(73) Assignee: Motorika Limited, Hamilton (BM)

( * ) Notice: Subject to any disclaimer, the term of this patent is extended or adjusted under 35 U.S.C. 154(b) by 843 days.

(21) Appl. No.: 12/918,078

(22) PCT Filed: Feb. 19, 2009

(86) PCT No.: PCT/IL2009/000198
§ 371 (c)(1),
(2), (4) Date: Aug. 18, 2010

(87) PCT Pub. No.: WO2009/104190
PCT Pub. Date: Aug. 27, 2009

(65) Prior Publication Data
US 2011/0004126 A1    Jan. 6, 2011

Related U.S. Application Data

(60) Provisional application No. 61/064,209, filed on Feb. 21, 2008.

(51) Int. Cl.
*A61B 5/103* (2006.01)
*G06F 19/00* (2011.01)
(Continued)

(52) U.S. Cl.
CPC ....... *G06F 19/3487* (2013.01); *G06F 19/3481* (2013.01); *G06Q 50/22* (2013.01); *G06Q 50/24* (2013.01)

(58) Field of Classification Search
CPC .... A61B 5/003; A61B 5/103; A61B 5/1071; A61B 5/4528
USPC ............................ 33/511, 512; 600/587, 595
See application file for complete search history.

(56) References Cited

U.S. PATENT DOCUMENTS 6,056,671 A  *  5/2000  Marmer ............................ 482/8
6,454,706 B1 *  9/2002  Pullman ............... A61B 5/4082
                                                          600/300

(Continued)

FOREIGN PATENT DOCUMENTS

| WO | WO 2006/082584 | 8/2006 |
| WO | WO 2007/131340 | 11/2007 |
| WO | WO 2009/104190 | 8/2009 |

OTHER PUBLICATIONS

International Search Report Dated Feb. 24, 2010 From the International Searching Authority Re.: Application No. PCT/IL2009/000198.

(Continued)

*Primary Examiner* — Sean Dougherty
*Assistant Examiner* — Daniel Cerioni

(57) ABSTRACT

A method for scoring one or more functional abilities of a patient that comprises exercising a patient according to an exercising pattern, using at least one sensor for sensing one or more manipulations of the patient during the exercising, and scoring the one or more functional abilities according to the sensed manipulations. The scoring is performed according to a visual rehabilitation evaluation scale for scoring the one or more functional abilities.

39 Claims, 11 Drawing Sheets
(3 of 11 Drawing Sheet(s) Filed in Color)

(51) Int. Cl.
*G06Q 50/22* (2012.01)
*G06Q 50/24* (2012.01)

(56) References Cited

U.S. PATENT DOCUMENTS

| | | | |
|---|---|---|---|
| 8,012,107 B2* | 9/2011 | Einav et al. | 601/5 |
| 8,112,155 B2* | 2/2012 | Einav et al. | 607/48 |
| 8,177,732 B2* | 5/2012 | Einav et al. | 601/5 |
| 2004/0147817 A1* | 7/2004 | Dewing et al. | 600/300 |
| 2005/0240086 A1* | 10/2005 | Akay | 600/300 |
| 2006/0195018 A1* | 8/2006 | Guillen | 600/300 |
| 2006/0277074 A1* | 12/2006 | Einav et al. | 705/3 |
| 2006/0293617 A1* | 12/2006 | Einav et al. | 601/33 |
| 2007/0179570 A1* | 8/2007 | De Taboada | A61H 7/006 607/88 |
| 2007/0265146 A1* | 11/2007 | Kowalczewski et al. | 482/92 |
| 2007/0299371 A1* | 12/2007 | Einav et al. | 601/5 |
| 2008/0004550 A1* | 1/2008 | Einav et al. | 601/33 |
| 2008/0070752 A1* | 3/2008 | Einav | 482/7 |
| 2008/0132383 A1* | 6/2008 | Einav et al. | 482/8 |
| 2008/0234113 A1* | 9/2008 | Einav | 482/66 |
| 2008/0234781 A1* | 9/2008 | Einav et al. | 607/48 |
| 2008/0242521 A1* | 10/2008 | Einav | 482/110 |
| 2009/0062698 A1* | 3/2009 | Einav et al. | 601/5 |
| 2009/0105787 A1* | 4/2009 | Kokones et al. | 607/59 |
| 2009/0221928 A1* | 9/2009 | Einav et al. | 600/544 |
| 2010/0049095 A1* | 2/2010 | Bunn et al. | 600/595 |

OTHER PUBLICATIONS

Gritsenko et al. "A Functional Electric Stimulation-Assisted Exercise Therapy System for Hemiplegic Hand Function", Archives of Physical Medicine and Rehabilitation, XP002568013, 85: 881-885, Jun. 2004. p. 882, r-h col. § 3—p. 883, 1-h col. § 2.

Williams et al. "Predicting Patient Scores Between the Functional Independence Measure and the Minimum Data Set: Development and Performance of a FIM-MDS 'Crosswalk'", Archives of Physical Medicine and Rehabilitation, XP002568014, 78: 48-54, Jan. 1997.

International Preliminary Report on Patentability Dated Sep. 2, 2010 From the International Bureau of WIPO Re. Application No. PCT/IL2009/000198.

\* cited by examiner

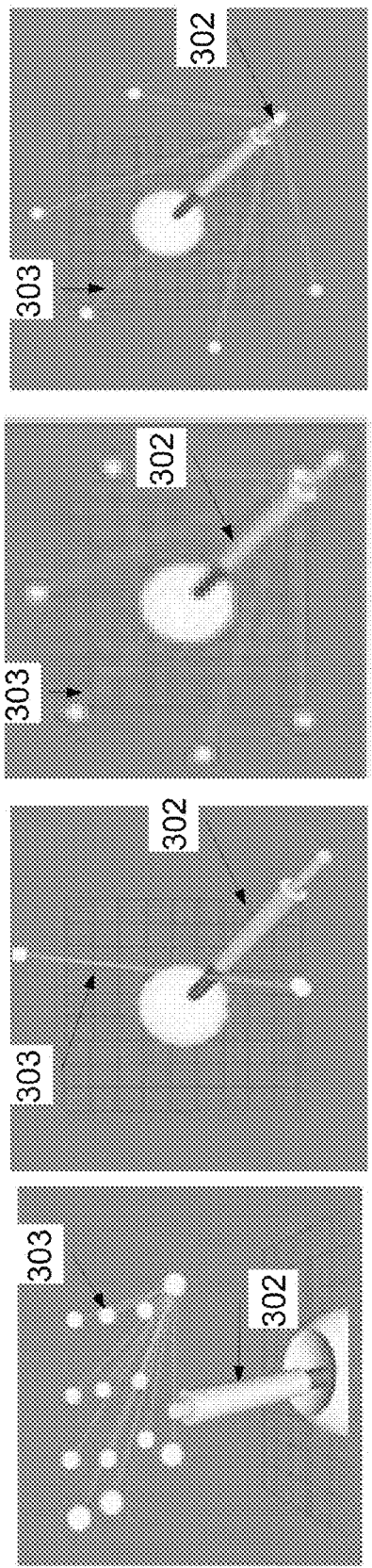
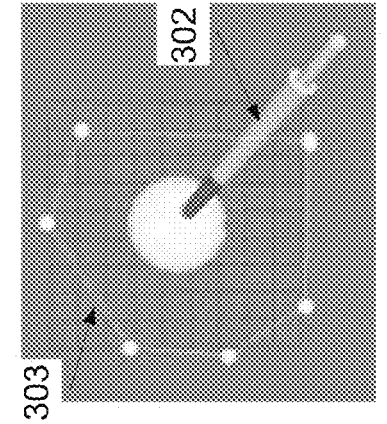
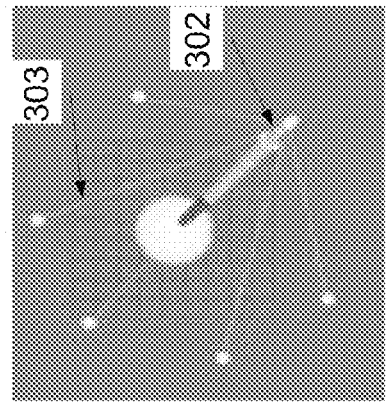
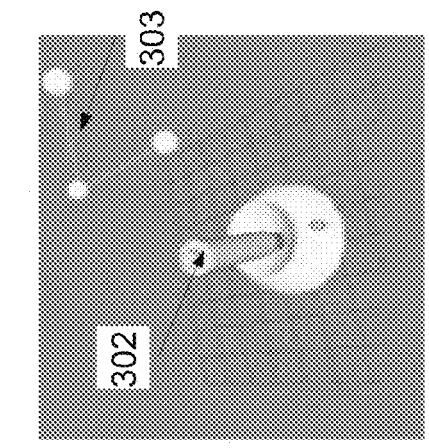
FIG. 2A  FIG. 2B  FIG. 2C  FIG. 2D  FIG. 2E  FIG. 2F  FIG. 2G

Fig. 6

| Patient | FM | FM_P | FM_D | ARAT | WT | WW | Motricity | Pinch | Grip | WROM | Fstar | Fvretical | FT_PE | FT_TE | FT_AE | ELB_PE | ELB_TE | ELB_AE | RWL_PE |
|---|---|---|---|---|---|---|---|---|---|---|---|---|---|---|---|---|---|---|---|
| 1 | 42 | 26 | 16 | 28 | 4.0 | 2.40 | 71 | 44.44 | 27.75 | 66.67 | 97.62 | 92.84 | 67.91 | 78.46 | 79.29 | 45.12 | 48.65 | 76.85 | 56.50 |
| 2 | 44 | 27 | 17 | 39 | 4.0 | 3.50 | 73 | 49.04 | 6.59 | 94.44 | 87.09 | 79.67 | 72.18 | 57.68 | 89.60 | 42.40 | 49.72 | 93.65 | 56.52 |
| 3 | 30 | 15 | 15 | 3 | 16.0 | 1.70 | 40 | 29.29 | 12.72 | 50.00 | 69.76 | 45.08 | 79.11 | 65.69 | 93.99 | 35.76 | 38.69 | 73.96 | 47.47 |
| 4 | 64 | 34 | 30 | 57 | 3.0 | 4.10 | 100 | 52.00 | 13.51 | 58.33 | 74.78 | 65.77 | 64.97 | 48.71 | 72.35 | 61.65 | 53.66 | 61.05 | 62.70 |
| 5 | 63 | 33 | 30 | 54 | 3.0 | 3.70 | 85 | 86.87 | 64.32 | 94.44 | 115.38 | 88.49 | 79.57 | 95.30 | 109.89 | 43.91 | 49.10 | 93.80 | 51.50 |
| 6 | 49 | 28 | 21 | 43 | 2.0 | 3.50 | 67 | 46.02 | 18.11 | 72.22 | 90.84 | 88.78 | 90.95 | 91.74 | 111.57 | 78.15 | 93.02 | 96.56 | 79.20 |
| 7 | 37 | 16 | 21 | 21 | 18.0 | 2.20 | 62 | 125.25 | 59.83 | 75.00 | 51.57 | 58.83 | 43.34 | 36.91 | 66.63 | 44.73 | 51.96 | 38.99 | 15.84 |
| 8 | 51 | 28 | 23 | 38 | 5.0 | 3.00 | 67 | 82.83 | 17.63 | 61.11 | 97.64 | 55.14 | 90.04 | 98.12 | 83.91 | 65.07 | 71.60 | 87.99 | 72.95 |
| 9 | 65 | 34 | 31 | 57 | 3.0 | 4.10 | 100 | 120.59 | 89.24 | 88.89 | 96.74 | 91.90 | 73.85 | 100.00 | 78.53 | 59.80 | 59.19 | 79.54 | 67.20 |
| 10 | 10 | 9 | 1 | 0 | 120.0 | 1.10 | 40 | 1.01 | 22.22 | 14.43 | 10.35 | 89.23 | 0.00 | 0.00 | 0.00 | 0.00 | 0.00 | 0.00 | 0.00 |
| 11 | 13 | 12 | 1 | 0 | 120.0 | 0.00 | 40 | 0.00 | 0.00 | 8.33 | 59.72 | 77.86 | 84.61 | 64.11 | 84.44 | 9.37 | 43.81 | 54.61 | 8.59 |
| 12 | 57 | 30 | 27 | 57 | 2.0 | 4.30 | 92 | 66.67 | 69.73 | 83.33 | 92.01 | 91.75 | 92.50 | 94.29 | 85.72 | 31.34 | 44.55 | 83.61 | 32.12 |
| 13 | 46 | 28 | 18 | 45 | 3.0 | 3.60 | 77 | 90.00 | 37.60 | 66.67 | 88.15 | 100.00 | 90.70 | 100.00 | 72.54 | 66.34 | 69.58 | 98.27 | 66.39 |
| 14 | 59 | 33 | 26 | 52 | 6.0 | 3.90 | 100 | 91.92 | 58.96 | 66.67 | 99.21 | 90.30 | 80.76 | 95.65 | 100.81 | 63.75 | 66.07 | 98.28 | 58.78 |
| 15 | 36 | 24 | 12 | 21 | 9.0 | 2.50 | 62 | 49.15 | 11.33 | 61.11 | 81.06 | 76.41 | 85.98 | 93.91 | 100.00 | 74.64 | 59.01 | 99.26 | 77.79 |
| 16 | 49 | 29 | 20 | 37 | 3.0 | 3.50 | 79 | 105.77 | 52.53 | 72.22 | 92.60 | 96.31 | 85.08 | 100.00 | 163.50 | 76.54 | 90.73 | 116.04 | 71.23 |
| 17 | 42 | 25 | 17 | 19 | 11.0 | 2.80 | 73 | 36.00 | 8.91 | 47.22 | 70.29 | 69.83 | 64.92 | 81.82 | 65.95 | 0.00 | 0.00 | 92.54 | 26.35 |
| 18 | 23 | 20 | 3 | 3 | 120.0 | 1.30 | 36 | 16.10 | 0.00 | 44.44 | 36.75 | 58.61 | 51.78 | 55.01 | 96.00 | 49.44 | 56.93 | 69.18 | 23.01 |
| 19 | 24 | 16 | 8 | 3 | 120.0 | 0.90 | 45 | 19.19 | 5.85 | 25.00 | 34.24 | 51.09 | 32.51 | 36.38 | 62.66 | 51.76 | 47.72 | 57.93 | 22.76 |
| 20 | 32 | 19 | 13 | 16 | 35.0 | 2.50 | 62 | 19.19 | 11.35 | 47.22 | 28.91 | 32.71 | 85.28 | 86.67 | 95.47 | 76.40 | 68.60 | 80.27 | 57.17 |
| 21 | 5 | 4 | 1 | 0 | 120.0 | 0.00 | 21 | 5.77 | 0.00 | 0.00 | 0.00 | 0.00 | 0.00 | 0.00 | 0.00 | 0.00 | 0.00 | 0.00 | 0.00 |
| 22 | 15 | 15 | 0 | 6 | 24.0 | 1.90 | 34 | 0.00 | 0.00 | 50.00 | 47.76 | 51.30 | 47.66 | 50.17 | 100.00 | 41.20 | 52.70 | 94.54 | 27.93 |
| 23 | 7 | 7 | 0 | 0 | 120.0 | 0.90 | 19 | 0.00 | 0.00 | 8.33 | 5.09 | 11.36 | 89.23 | 79.99 | 59.67 | 0.00 | 0.00 | 0.00 | 4.82 |
| 24 | 62 | 33 | 29 | 54 | 2.0 | 4.70 | 100 | 121.21 | 58.78 | 86.11 | 64.88 | 92.55 | 71.92 | 77.03 | 71.76 | 67.47 | 70.13 | 78.87 | 69.91 |
| 25 | 7 | 7 | 0 | 0 | 120.0 | 0.70 | 19 | 0.00 | 0.00 | 0.00 | 7.51 | 4.49 | 0.00 | 0.00 | 12.15 | 2.30 | 12.42 | 3.56 | 7.85 |
| 26 | 63 | 34 | 29 | 57 | 1.0 | 4.90 | 100 | 70.80 | 66.34 | 66.67 | 67.24 | 88.78 | 80.37 | 89.66 | 100.04 | 78.34 | 81.20 | 103.44 | 79.32 |
| 27 | 59 | 31 | 28 | 57 | 1.0 | 4.40 | 92 | 91.00 | 55.49 | 86.11 | 64.12 | 89.00 | 78.20 | 77.08 | 83.26 | 57.41 | 54.27 | 90.31 | 69.51 |
| 28 | 21 | 17 | 4 | 8 | 120.0 | 1.70 | 56 | 30.77 | 7.03 | 55.56 | 40.61 | 60.06 | 63.85 | 69.39 | 68.73 | 35.25 | 28.73 | 66.87 | 35.24 |
| 29 | 25 | 17 | 8 | 22 | 19.0 | 2.50 | 77 | 61.62 | 9.54 | 63.89 | 39.37 | 50.07 | 61.23 | 48.61 | 68.69 | 4.80 | 27.93 | 45.86 | 26.25 |
| 30 | 9 | 8 | 1 | 0 | 120.0 | 1.40 | 35 | 5.08 | 0.00 | 8.33 | 12.12 | 18.52 | 32.52 | 39.20 | 39.44 | 36.00 | 32.58 | 45.12 | 8.13 |
| 31 | 53 | 29 | 24 | 41 | 3.0 | 3.50 | 87 | 103.57 | 32.82 | 61.11 | 61.99 | 95.51 | 90.69 | 94.77 | 100.00 | 83.49 | 87.34 | 88.22 | 81.14 |
| 32 | 64 | 34 | 30 | 57 | 1.0 | 4.70 | 92 | 79.66 | 36.43 | 69.44 | 60.15 | 84.95 | 83.89 | 95.74 | 103.37 | 77.66 | 81.71 | 94.76 | 64.85 |
| 33 | 53 | 33 | 20 | 30 | 5.0 | 3.40 | 81 | 26.26 | 11.22 | 55.56 | 66.31 | 89.44 | 82.44 | 97.22 | 111.22 | 70.98 | 87.73 | 107.76 | 64.86 |
| 34 | 11 | 10 | 1 | 0 | 120.0 | 1.40 | 45 | 7.96 | 2.36 | 19.44 | 13.76 | 0.29 | 0 | 0.00 | 0.00 | 0.00 | 29.33 | 75.64 |  |
| 35 | 50 | 34 | 16 | 16 | 4.0 | 3.40 | 87 | 6.06 | 0.00 | 55.56 | 67.75 | 92.11 | 86.72 | 100.00 | 100.89 | 79.49 | 92.61 | 105.76 | 75.64 |
| 36 | 64 | 30 | 30 | 56 | 1.00 | 4.60 | 100 | 95.16 | 157.69 | 83.33 | 64.20 | 91.03 | 85.01 | 100.00 | 100.00 | 82.16 | 94.06 | 96.82 | 79.18 |
| 37 | 24 | 17 | 7 | 7 | 120.00 | 1.40 | 56 | 11.76 | 4.48 | 33.60 | 18.47 | 44.21 | 27.18 | 32.12 | 41.15 | 4.59 | 28.73 | 20.10 | 14.20 |
| 38 | 6 | 6 | 0 | 0 | 120.00 | 0.00 | 19 | 0.00 | 0.00 | 0.00 | 1.93 | 0.58 | 0.00 | 0.00 | 0.00 | 0.00 | 45.86 | 12.73 | 2.91 |
| 39 | 64 | 34 | 30 | 57 | 1.00 | 4.70 | 93 | 61.33 | 124.04 | 83.33 | 64.93 | 89.94 | 78.44 | 93.90 | 89.65 | 78.82 | 91.53 | 93.62 | 73.57 |
| 40 | 4 | 4 | 0 | 0 | 120.00 | 0.00 | 1 | 0.00 | 0.00 | 0.00 | 0.42 | 0.00 | 0.00 | 0.00 | 0.00 | 0.00 | 0.00 | 0.00 | 0.00 |
| 41 | 63 | 34 | 29 | 57 | 2.00 | 4.40 | 85 | 56.80 | 81.00 | 77.78 | 61.61 | 81.55 | 78.03 | 86.59 | 105.34 | 60.91 | 57.99 | 102.48 | 70.89 |
| 42 | 58 | 31 | 27 | 56 | 1.3 | 4.5 | 77 | 96.97 | 51.73 | 66.67 | 60.71 | 94.07 | 66.56 | 76.12 | 87.08 | 77.32 | 92.52 | 99.98 | 72.16 |
| 43 | 5 | 5 | 0 | 3 | 120 | 0 | 10 | 0.00 | 0.00 | 0.00 | 1.33 | 0.65 | 41.92 | 57.90 | 28.93 | 33.91 | 36.10 | 33.16 | 12.13 |
| 44 | 10 | 10 | 0 | 3 | 120 | 1.3 | 35 | 13.13 | 3.66 | 5.56 | 21.19 | 42.04 | 0.00 | 0.00 | 0.00 | 0.61 | 0.35 | 0.55 | 0.00 |
| 45 | 62 | 34 | 28 | 45 | 2.3 | 4.1 | 93 | 145.19 | 80.66 | 116.67 | 64.51 | 92.11 | 76.30 | 92.54 | 96.97 | 72.30 | 75.14 | 84.03 | 73.82 |
| 46 | 63 | 33 | 30 | 57 | 1.2 | 4.7 | 92 | 106.06 | 79.48 | 80.56 | 62.67 | 91.03 | 77.19 | 98.59 | 106.39 | 68.33 | 80.61 | 106.17 | 68.60 |
| 47 | 5 | 5 | 0 | 0 | 120 | 0 | 84 | 0.00 | 36.04 | 0.00 | 2.09 | 0.00 | 83.28 | 100.00 | 90.13 | 0.00 | 0.00 | 0.00 | 0.00 |
| 48 | 58 | 28 | 30 | 51 | 1.5 | 4.6 | 15 | 95.96 | 0.00 | 69.44 | 53.26 | 65.70 | 0.00 | 0.00 | 0.00 | 70.69 | 84.55 | 105.33 | 72.79 |
| 49 | 5 | 5 | 0 | 0 | 120 | 1 | 67 | 0.00 | 0.00 | 11.11 | 4.28 | 7.38 | 0.00 | 0.00 | 0.00 | 0.00 | 0.00 | 0.00 | 0.00 |
| 50 | 44 | 26 | 18 | 29.5 | 0 | 3.4 | 67 | 44.07 | 23.70 | 38.89 | 42.61 | 43.27 | 90.53 | 70.00 | 59.23 | 54.86 | 45.70 | 65.35 | 49.15 |
| 51 | 8 | 8 | 0 | 0 | 120 | 0.8 | 19 | 0.00 | 0.00 | 2.78 | 17.67 | 40.38 | 0.00 | 0.00 | 0.00 | 0.00 | 0.00 | 0.00 | 0.00 |
| 52 | 50 | 30 | 20 | 17 | 13.3 | 2.4 | 67 | 30.30 | 13.17 | 58.33 | 63.76 | 63.24 | 58.40 | 58.75 | 85.96 | 77.42 | 74.95 | 84.18 | 0.00 |
| 53 | 11 | 9 | 2 | 3 | 120 | 0.9 | 40 | 4.81 | 10.89 | 2.78 | 12.33 | 20.91 | 0.00 | 0.00 | 0.00 | 0.17 | 37.24 | 12.04 | 15.50 |

|  | FM | FM_P | FM_D | ARAT | WT | WW | Motricity |
|---|---|---|---|---|---|---|---|
| Pinch | 0.82 | 0.68 | 0.85 | 0.84 | -0.78 | 0.80 | 0.80 |
| Grip | 0.74 | 0.68 | 0.78 | 0.79 | -0.61 | 0.74 | 0.70 |
| WROM | 0.90 | 0.89 | 0.88 | 0.85 | -0.88 | 0.88 | 0.89 |
| Fstar | 0.83 | 0.85 | 0.78 | 0.76 | -0.85 | 0.77 | 0.80 |
| Fvretical | 0.87 | 0.91 | 0.82 | 0.81 | -0.82 | 0.86 | 0.87 |
| FT_PE | 0.77 | 0.79 | 0.73 | 0.70 | -0.80 | 0.77 | 0.75 |
| FT_TE | 0.82 | 0.84 | 0.78 | 0.75 | -0.81 | 0.80 | 0.78 |
| FT_AE | 0.77 | 0.81 | 0.72 | 0.67 | -0.79 | 0.75 | 0.74 |
| ELB_PE | 0.83 | 0.84 | 0.79 | 0.73 | -0.78 | 0.79 | 0.75 |
| ELB_TE | 0.79 | 0.81 | 0.75 | 0.71 | -0.74 | 0.76 | 0.74 |
| ELB_AE | 0.84 | 0.88 | 0.78 | 0.75 | -0.87 | 0.84 | 0.82 |
| RWL_PE | 0.90 | 0.92 | 0.87 | 0.84 | -0.89 | 0.88 | 0.85 |
| RWL_TE | 0.86 | 0.85 | 0.83 | 0.76 | -0.82 | 0.81 | 0.81 |
| RWL_AE | 0.88 | 0.90 | 0.84 | 0.81 | -0.93 | 0.88 | 0.84 |
| RSL_PE | 0.87 | 0.88 | 0.84 | 0.81 | -0.85 | 0.85 | 0.83 |
| RSL_TE | 0.86 | 0.86 | 0.84 | 0.80 | -0.82 | 0.84 | 0.83 |
| RSL_AE | 0.85 | 0.87 | 0.80 | 0.80 | -0.89 | 0.85 | 0.82 |
| HAB_PE | 0.81 | 0.82 | 0.78 | 0.75 | -0.78 | 0.79 | 0.76 |
| HAB_TE | 0.80 | 0.82 | 0.76 | 0.73 | -0.80 | 0.79 | 0.76 |
| HAB_AE | 0.87 | 0.88 | 0.82 | 0.79 | -0.90 | 0.87 | 0.85 |

FIG. 7

|  | FM | FM_P | FM_D | Wolf |
|---|---|---|---|---|
| (Constant) | 3.012 | 3.418 | -2.779 | 0.446 |
| Pinch | 0 | 0 | 0 | 0 |
| Grip | 0.225 | 0 | 0.176 | 0.017 |
| WROM | 0.208 | 0.105 | 0.138 | 0.018 |
| F Vertical | 0 | 0.086 | 0 | 0 |
| Fstar | 0.234 | 0 | 0.140 | 0.01 |
| FT | 0 | 0 | 0 | 0 |
| ELB | 0 | 0 | 0 | 0 |
| RWL | 0 | 0.140 | 0 | 0 |
| RSL | 0.132 | 0 | 0 | 0.009 |
| HAB | 0.000 | 0 | 0 | 0 |
| $R^2$ | 0.85 | 0.85 | 0.78 | 0.84 |
| ADJ-$R^2$ | 0.83 | 0.83 | 0.76 | 0.82 |

FIG. 8

| | Pinch | Grip | WROM | Fstar | Fvretical | FT_PE | FT_TE | FT_AE | ELB_PE | ELB_TE | ELB_AE | RWL_PE | RWL_TE | RWL_AE | RSL_PE | RSL_TE | RSL_AE | HAB_PE | HAB_TE | HAB_AE |
|---|---|---|---|---|---|---|---|---|---|---|---|---|---|---|---|---|---|---|---|---|
| Pinch | 1.00 | 0.76 | 0.84 | 0.68 | 0.74 | 0.60 | 0.66 | 0.61 | 0.66 | 0.64 | 0.64 | 0.73 | 0.75 | 0.69 | 0.74 | 0.75 | 0.66 | 0.64 | 0.62 | 0.66 |
| Grip | 0.76 | 1.00 | 0.71 | 0.52 | 0.63 | 0.48 | 0.57 | 0.49 | 0.56 | 0.57 | 0.53 | 0.61 | 0.64 | 0.60 | 0.62 | 0.64 | 0.58 | 0.60 | 0.58 | 0.59 |
| WROM | 0.84 | 0.71 | 1.00 | 0.83 | 0.86 | 0.75 | 0.78 | 0.80 | 0.75 | 0.72 | 0.83 | 0.83 | 0.81 | 0.86 | 0.80 | 0.79 | 0.82 | 0.74 | 0.74 | 0.83 |
| Fstar | 0.68 | 0.52 | 0.83 | 1.00 | 0.88 | 0.79 | 0.80 | 0.81 | 0.68 | 0.66 | 0.84 | 0.79 | 0.73 | 0.84 | 0.74 | 0.71 | 0.78 | 0.66 | 0.66 | 0.80 |
| Fvretical | 0.74 | 0.63 | 0.86 | 0.88 | 1.00 | 0.79 | 0.83 | 0.84 | 0.76 | 0.78 | 0.87 | 0.84 | 0.84 | 0.86 | 0.80 | 0.79 | 0.81 | 0.75 | 0.76 | 0.84 |
| FT_PE | 0.60 | 0.48 | 0.75 | 0.79 | 0.79 | 1.00 | 0.96 | 0.90 | 0.77 | 0.74 | 0.86 | 0.82 | 0.77 | 0.85 | 0.76 | 0.72 | 0.78 | 0.73 | 0.74 | 0.81 |
| FT_TE | 0.66 | 0.57 | 0.78 | 0.80 | 0.83 | 0.96 | 1.00 | 0.90 | 0.81 | 0.78 | 0.89 | 0.86 | 0.82 | 0.88 | 0.82 | 0.78 | 0.82 | 0.79 | 0.80 | 0.86 |
| FT_AE | 0.61 | 0.49 | 0.80 | 0.81 | 0.84 | 0.90 | 0.90 | 1.00 | 0.82 | 0.82 | 0.92 | 0.86 | 0.82 | 0.87 | 0.81 | 0.76 | 0.82 | 0.76 | 0.77 | 0.83 |
| ELB_PE | 0.66 | 0.56 | 0.75 | 0.68 | 0.76 | 0.77 | 0.81 | 0.82 | 1.00 | 0.93 | 0.85 | 0.93 | 0.92 | 0.85 | 0.91 | 0.90 | 0.85 | 0.87 | 0.89 | 0.80 |
| ELB_TE | 0.64 | 0.57 | 0.72 | 0.66 | 0.78 | 0.74 | 0.78 | 0.82 | 0.93 | 1.00 | 0.84 | 0.88 | 0.90 | 0.82 | 0.88 | 0.90 | 0.83 | 0.89 | 0.89 | 0.78 |
| ELB_AE | 0.64 | 0.53 | 0.83 | 0.84 | 0.87 | 0.86 | 0.89 | 0.92 | 0.85 | 0.84 | 1.00 | 0.89 | 0.86 | 0.95 | 0.84 | 0.81 | 0.89 | 0.80 | 0.82 | 0.93 |
| RWL_PE | 0.73 | 0.61 | 0.83 | 0.79 | 0.84 | 0.82 | 0.86 | 0.82 | 0.93 | 0.88 | 0.89 | 1.00 | 0.91 | 0.92 | 0.95 | 0.92 | 0.91 | 0.91 | 0.92 | 0.90 |
| RWL_TE | 0.75 | 0.64 | 0.81 | 0.73 | 0.84 | 0.77 | 0.82 | 0.82 | 0.92 | 0.90 | 0.86 | 0.91 | 1.00 | 0.87 | 0.88 | 0.93 | 0.84 | 0.83 | 0.88 | 0.83 |
| RWL_AE | 0.69 | 0.60 | 0.86 | 0.84 | 0.86 | 0.85 | 0.88 | 0.87 | 0.85 | 0.82 | 0.95 | 0.92 | 0.87 | 1.00 | 0.89 | 0.86 | 0.96 | 0.85 | 0.87 | 0.97 |
| RSL_PE | 0.74 | 0.62 | 0.80 | 0.74 | 0.80 | 0.76 | 0.82 | 0.81 | 0.91 | 0.88 | 0.84 | 0.95 | 0.88 | 0.89 | 1.00 | 0.96 | 0.93 | 0.93 | 0.93 | 0.87 |
| RSL_TE | 0.75 | 0.64 | 0.79 | 0.71 | 0.79 | 0.72 | 0.78 | 0.76 | 0.90 | 0.90 | 0.81 | 0.92 | 0.93 | 0.86 | 0.96 | 1.00 | 0.89 | 0.91 | 0.92 | 0.83 |
| RSL_AE | 0.66 | 0.58 | 0.82 | 0.78 | 0.81 | 0.78 | 0.82 | 0.82 | 0.85 | 0.83 | 0.89 | 0.91 | 0.84 | 0.96 | 0.93 | 0.89 | 1.00 | 0.87 | 0.90 | 0.91 |

Intracorrelation- between RS scores

SYSTEM AND A METHOD FOR SCORING FUNCTIONAL ABILITIES OF A PATIENT

RELATED APPLICATIONS

This application is a National Phase of PCT Patent Application No. PCT/IL2009/000198 having International filing date Feb. 19, 2009, which claims the benefit of U.S. Provisional Patent Application No. 61/064,209, filed on Feb. 21, 2008. The contents of the above Applications are all incorporated herein by reference.

FIELD AND BACKGROUND OF THE INVENTION

The present invention, in some embodiments thereof, relates to a method and a system for evaluating a physiological ability of a patient and, more particularly, but not exclusively, to a method and a system for evaluating one or more functional abilities, such as neuromuscular abilities, of a patient.

After an accident or a stroke, a patient often need a rehabilitation process in an attempt to recapture some or all of the body function damaged in the accident or the stroke. Such rehabilitation may include a physical rehabilitation and/or a cognitive rehabilitation. During the physical rehabilitation, damaged or unused muscles, nerves and/or joints are brought back to full or partial functioning. During the cognitive rehabilitation, the cognitive ability to control the body is restored. In some cases, the patient needs to be trained in modified functionalities or even in new functionalities, for example, in the use of an artificial limb.

Currently, functional rehabilitation is mostly provided by personal attention of a physical therapist that exercises a patient in the performance of physiotherapy trainings. Furthermore, the current practice of a clinical assessment of such a functional rehabilitation remains mainly an assessment that is given by a clinician, a physiotherapist, or an occupational therapist.

During the last decade, different systems and devices have been developed for automating rehabilitation process exercises. For example, U.S. Patent Application No. 2006/0229164, issued on Oct. 12, 2006, describes an exercise apparatus that comprises a resistance element, operative to supply a resistance to movement by a user of the apparatus and an actuator module which is operatively connected to the resistance element and operative to vary a resistance perceived by the user without changing the resistance element.

Another device for automating rehabilitation process exercises is described in U.S. Patent Application No. 2006/0293617, issued on Dec. 28, 2006 that discloses a rehabilitation apparatus with at least three degrees of freedom of motion, comprising: a plurality of brakes; a motor, wherein the motor is operationally connected to the brakes; a plurality of surfaces, wherein each of a plurality of the surfaces correlates to a brake; and, wherein when the motor is activated, the brakes are selectively advanced to make contact with the surfaces causing friction between the brakes and the surfaces and thus causing variable resistance in the three degrees of freedom to the apparatus based on the extent of advancement of the brakes. Both U.S. Patent Applications are incorporated herein by reference.

SUMMARY OF THE INVENTION

According to an aspect of some embodiments of the present invention there is provided According to an aspect of some embodiments of the present invention there is provided a method for scoring one or more functional abilities of a patient. The method comprises: a) exercising a patient according to an exercising pattern, b) using at least one sensor for sensing at least one manipulation of the patient during the exercising, and c) scoring the one or more functional abilities according to the at least one sensed manipulation, the scoring being performed according to a visual rehabilitation evaluation scale for scoring the one or more functional abilities.

Optionally, the method further comprises generating a single functional evaluation score according to the scoring.

Optionally, the method further comprises diagnosing the patient with regard to the functional ability according to the visual rehabilitation evaluation scale.

Optionally, the method further comprises using the visual rehabilitation evaluation scale for monitoring a therapy given to the patient with regard to the functional ability.

More optionally, the functional evaluation score is a neuromuscular evaluation.

Optionally, the scoring comprises giving a rehabilitation score to the functional ability, the exercising pattern comprising a plurality of rehabilitation exercises.

Optionally, the exercising pattern define a member selected from a group consisting of: a Pinch exercise, a Grip exercise, a force-star (F-Star) exercise, a wrist range of motion (WROM) exercise, a forward thrust (FT) exercise, an elbow extension/flexion (ELB) exercise, a reach waist level (RWL) exercise, a reach shoulder level (RSL) exercise, and a horizontal abduction (HAB) exercise.

Optionally, the visual rehabilitation evaluation scale comprising a member selected from a group consisting of: an action research arm test (ARAT), a stroke impact scale (SIS), Fugl-Meyer assessment (FMA), motor assessment scale (MAS), wolf motor function test (WMFT), motor status score for the Upper Extremity (MSS), manual function test (MFT).

Optionally, the method further comprises repeating a) and b) after the c) with an adjusted exercising pattern and adjusting the scoring according to the at least one sensed manipulation performed of the repeated b), the exercising pattern being adjusted according to the scoring.

More optionally, the adjusted exercising pattern comprises at least one rehabilitation evaluation exercise for evaluating the progress of the patient with regard to the functional ability.

More optionally, the evaluating comprises evaluating a rehabilitation re-evaluation score according to the at least one sensed manipulation.

More optionally, the evaluating comprises evaluating a progress of the patient according to the at least one sensed manipulation.

More optionally, the adjusting allows the overcoming at least one of a ceiling effect and a floor effect.

More optionally, the one or more functional abilities comprises a plurality of abilities, the exercising pattern being adjusted according to scoring at least some of the plurality of abilities according to the score of at least one of the others of the plurality of abilities.

Optionally, the scoring is performed according to medical information pertaining to the patient.

More optionally, the medical information is selected from a member of a group consisting of: a laboratory result, a therapeutic procedure record, a clinical evaluation, age, gender, a medical condition, genetic information, a patient medical record, a metabolism related data, a blood pressure, a sensitivity, an allergy, a population relevance, a treatment, a treatment outcome, an epidemiologic classification, comorbidity, a treatment history.

Optionally, the at least one manipulation comprises a three dimensional (3D) manipulation.

Optionally, at least one of the scored functional ability is scored with a member selected from a group consisting of: a quality of movement score, active range of motion (ROM) score, resistance score, passive ROM score, a smoothness score, a path efficiency score, a motion direction score, and a resistance to movement score.

Optionally, the exercising comprises a member selected from a group consisting of: applying forces, pushing forces, assisting forces, reminding forces, responding forces, and resisting forces during the at least one manipulation.

Optionally, the exercising comprises adjusting the exercising pattern according to the at least one manipulation during the sensing.

More optionally, the adjusting is performed according to a member selected from a group consisting of: the path of the at least one sensed manipulation, the velocity of the at least one sensed manipulation, the force of the at least one sensed manipulation, a compression to at least one previously sensed performance activity.

More optionally, the method further comprises evaluating physiological limitations of the patient according to the functional evaluation score.

More optionally, the physiological limitations comprise a limitation selected from a group comprising: a motor limitation, a cognitive limitation and/or a speech limitation.

More optionally, the generating comprises calculating the motor functional evaluation score according to medical information pertaining to the patient.

According to an aspect of some embodiments of the present invention there is provided a method for evaluating a functional performance of a patient. The method comprises: a) exercising a patient according to at least one functional exercise, b) measuring at least one manipulation of the patient during the exercising, c) evaluating a functional ability according to the at least one measured manipulation, d) defining at least one new functional exercise according to the evaluation, and e) repeating a)-c) wherein the functional exercise is the new functional exercise.

Optionally, the defining comprises adjusting the at least one functional exercise for producing the at least one new functional exercise.

Optionally, the defining comprises matching the at least one measured manipulation with a plurality of predefined manipulation patterns.

More optionally, the plurality of predefined manipulation patterns are arranged in a hierarchical database.

Optionally, the at least one functional exercise is configured for evaluating the functional ability, the at least one new functional exercise being configured for evaluating the progress of the patient with regard to the functional ability.

Optionally, the defining comprises matching between a time-lapse measured during the at least one functional exercise and a previously measured time-lapse taken during at least one respective functional exercise performed by the patient.

According to an aspect of some embodiments of the present invention there is provided a system for evaluating one or more functional abilities of a patient. The system comprises a database configured for hosting at least one preliminary exercising pattern and a plurality of adjusted exercising patterns and an adaptive training unit configured for exercising a patient according to the at least one preliminary exercising pattern and providing a preliminary evaluation of the one or more functional abilities according to the exercising. The adaptive training unit is configured for selecting at least one of the plurality of adjusted exercising patterns according to the preliminary evaluation and exercising the patient according to the selected adjusted exercising pattern.

Optionally, the preliminary evaluation is a rehabilitation evaluation and each the adjusted exercising pattern being a rehabilitation re-evaluation exercise.

According to an aspect of some embodiments of the present invention there is provided a system for evaluating patient performances. The system comprises a database configured for hosting at least one visual rehabilitation evaluation scale for rating a functional ability, a training unit configured for exercising a patient according to at least one exercising pattern, and an evaluation unit configured for scoring the exercising according to the at least one visual rehabilitation evaluation scale.

Optionally, the database is configured for hosting a plurality of visual rehabilitation evaluation scales, further comprising a user interface configured for allowing the operator of the system to select one of the plurality of visual rehabilitation evaluation scales, the evaluation unit being configured for scoring the exercising according to the selected visual rehabilitation evaluation scale.

Optionally, the at least one visual rehabilitation evaluation scale comprises a member selected from a group consisting of: an action research arm test (ARAT), a stroke impact scale (SIS), Fugl-Meyer assessment (FMA), motor assessment scale (MAS), wolf motor function test (WMFT), motor status score for the Upper Extremity (MSS), manual function test (MFT).

Optionally, the evaluation unit is configured for measuring time during the exercising, the scoring being performed according to the measured time.

Unless otherwise defined, all technical and/or scientific terms used herein have the same meaning as commonly understood by one of ordinary skill in the art to which the invention pertains. Although methods and materials similar or equivalent to those described herein may be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention may involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a schematic illustration of an evaluation system for evaluating patient performances, according to some embodiments of the present invention;

FIGS. 2A-2G depict schematic illustrations of exercises which are performed by an exemplary stick, which is part of an exemplary training unit, according to some embodiments of the present invention;

FIG. 3 is a flowchart of a method for generating a performance score for a patient according to her functional performances according to some embodiments of the present invention;

FIG. 4 is a multiple column chart that describes the distribution of scores of experimental patients in the set of exercises of an exemplary exercising pattern;

FIG. 5 is a flowchart of a method for adaptive evaluation of a functional performance of a patient, according to some embodiments of the present invention;

FIG. 6 is a table that summarizes the measurements of 53 selected patients which where taken using the training unit of the evaluation system which is described in FIG. 1;

FIG. 7 is a table that includes a set of correlation values, each allows the conversion of one or more of the measurements which are taken by the system to a score or a sub-score of a visual rehabilitation evaluation scale;

FIG. 8 is a table that includes a set of reduced correlation values that is based on a linear regression of the values of the table that is depicted in FIG. 7;

FIG. 9 is a table that depicts a set of intra-correlation values;

FIG. 10A is a schematic illustration of vectors that comprise a force star exercise for the left hand and the right hand;

FIG. 10B is a schematic illustration of four different training vectors of a force-star (F-star) exercise;

Figure 11A:
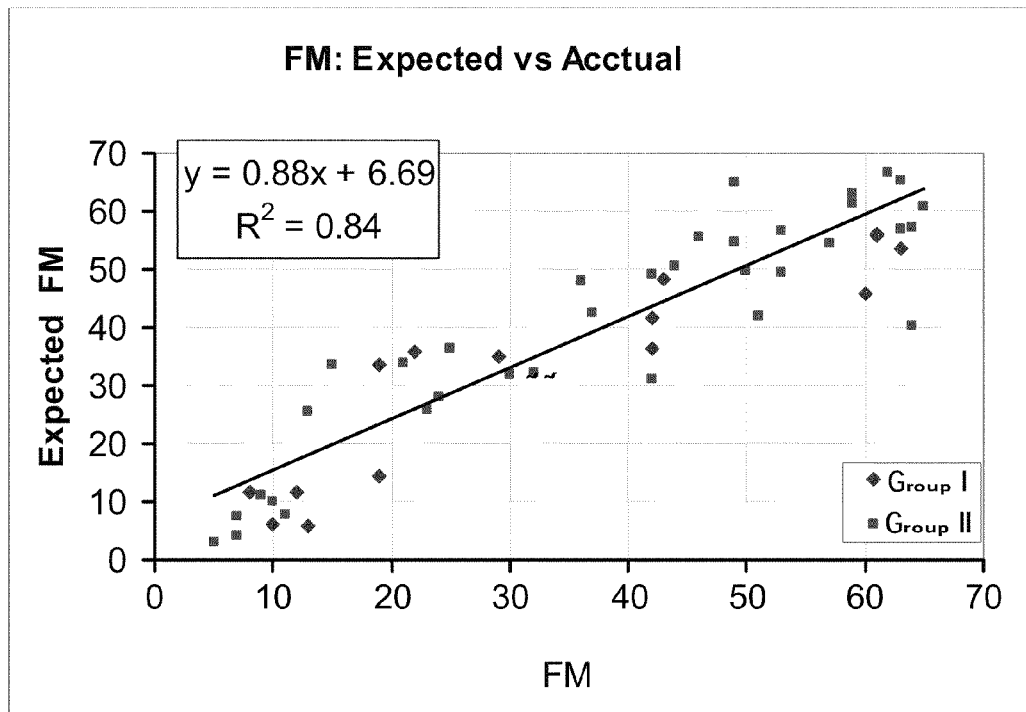
Figure 11B:
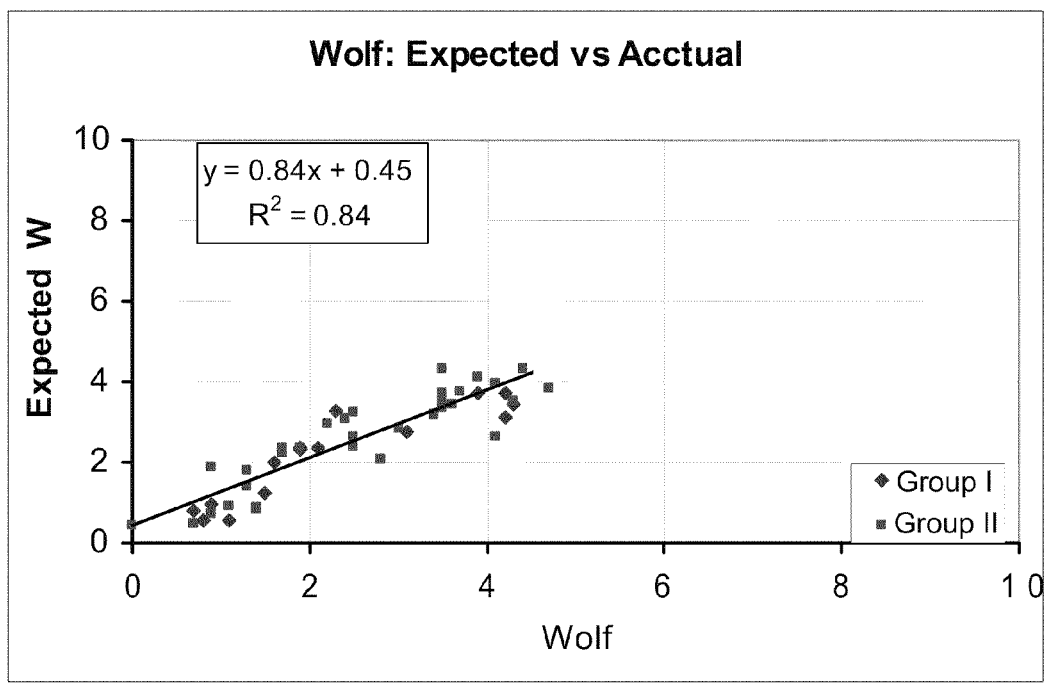
Figure 12:
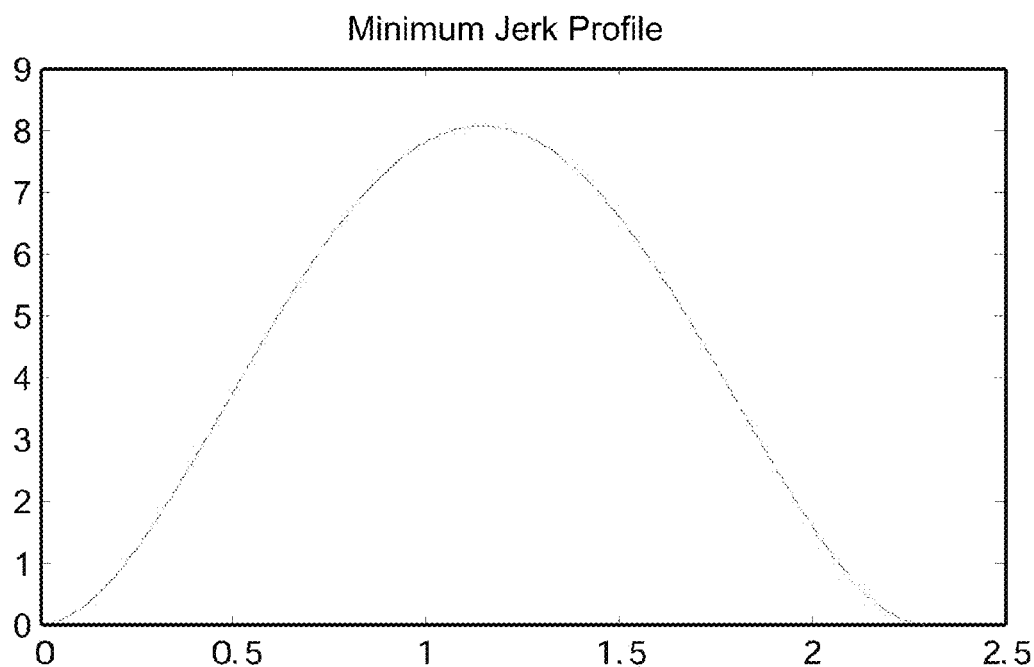
Figure 13:
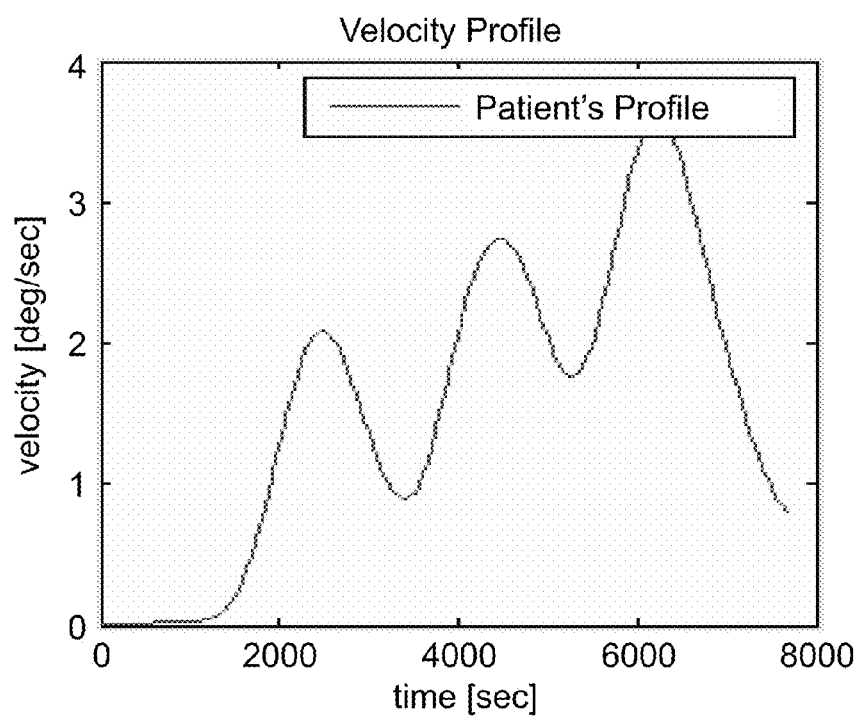

FIGS. 11A and 11B are charts that respectively depict the expected FMA scores and WMFT scores around a regression line that is based on the actual FMA scores and WMFT scores;

FIG. 12 is a graph depicting an ideal velocity profile of an estimated motion of a lever of a training unit between two points by a healthy patient; and FIG. 13 is a graph depicting an actual velocity profile for a motion of a lever of a training unit that is manipulated between two points during the performance of an exercise by an actual patient.

DESCRIPTION OF EMBODIMENTS OF THE INVENTION

The present invention, in some embodiments thereof, relates to a method and a system for evaluating a physiological ability of a patient and, more particularly, but not exclusively, to a method and a system for evaluating one or more functional abilities, such as a neuromuscular ability, of a patient.

Some embodiments of the present invention disclose a method and a system for evaluating functional performances of a patient, optionally in an adaptive manner. The evaluation, which is performed automatically, is designed to be correlated with a known visual rehabilitation evaluation scale, such as an action research arm test (ARAT), a stroke impact scale (SIS), Fugl-Meyer assessment (FMA), motor assessment scale (MAS), wolf motor function test (WMFT), motor status score for the Upper Extremity (MSS), manual function test (MFT).

Optionally, the evaluation is performed by an evaluation system that exercises the patient according to a certain exercising pattern and measures manipulations that the patient performs during the exercising. Optionally, the evaluation system defines the exercising pattern in an adaptive manner, optionally according to one or more previous evaluations and/or current medical information about the patient. Optionally, the exercising pattern is selected from a hierarchical database that hosts a number of exercising patterns. Optionally, the evaluation system is used for performing a rehabilitation evaluation and/or re-evaluation exercises.

Some embodiments of the present invention are related to a set of exercises that is defined according to predefined clinician requirements, which are optionally defined according to the medical condition of the patient. Optionally, a relatively high degree of lack of correlation is achieved among the functional abilities which are scored by the evaluating the performances which are measured during each one of the exercises. In such an embodiment, the patient is exercised for a relatively short time. Exercises are selected in a manner that they evaluate a set of functional abilities that is defined according to the predefined clinician requirements. The predefined clinician requirements allow the operator and/or the system to adjust a set of exercises that is adjusted according to the capabilities of the patient and/or her previous performances. Optionally, the predefined clinician requirements define a set of functional abilities and a level of certainty for each one of the set of functional abilities. In such an embodiment, if the required level of certainty is relatively high, the set of exercises may include a number of exercises for the same functional ability. However, if the level of certainty is relatively low, the set of exercises may include fewer exercises, optionally one. Optionally, the predefined clinician requirements define a set of constraints and the set of exercises includes the minimum number of exercises that fulfills set of constraints. Optionally, a minimum number of exercises are selected in a manner that a relatively high degree of lack of correlation exists between them, optionally as described below. In such a manner, the set of exercises may take less time than a set of exercises that includes a number of exercises that may be used for evaluating similar functional abilities.

Some embodiments of the present invention disclose a method for evaluating one or more functional abilities of a patient. The method comprises setting an exercising pattern for the patient and using one or more sensors for sensing the manipulations she performs while exercising according to the exercising pattern. One or more functional abilities of the patient are scored according to the sensed manipulations. These scores may be correlated with a manual rehabilitation evaluation scale that scores the one or more functional abilities. In one embodiment of the present invention, the exercising pattern includes a set of exercises that is selected in order to shorten the period that is needed in order to provide an evaluation that may be correlated with the manual rehabilitation evaluation scale.

Some embodiments of the present invention are related to evaluating one or more functional abilities of a patient without using a cognitive model of the brain or any other mapping of brain activities. In such an embodiment, rehabilitation and rehabilitation evaluations may be based and/or adjusted according to measurements of manipulations, which are performed by the patient during a rehabilitation exercise or test. As no cognitive model or any other mapping is used, the embodiments of the present invention may adjust and/or generate exercising patterns according to the actual performances of the patient that may be affected by various factors, which are not mapped on a cognitive model, such as fear from the training unit and comorbidity.

Some embodiments of the present invention disclose a system for evaluating one or more functional abilities of a patient. The system includes a database that hosts one or more preliminary exercising patterns, such as rehabilitation evaluation patterns and a number of adjusted exercising patterns, such as rehabilitation re-evaluation exercising patterns. The system further includes an adaptive training unit that exercises a patient according to one of the preliminary exercising patterns and provides a preliminary evaluation pertaining to the one or more functional abilities of the patient according to her performances during the exercises. Optionally, the adaptive training unit is designed for selecting one or more of the adjusted exercising patterns according to the preliminary evaluation and for exercising the patient according to the selected adjusted exercising pattern.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Figure 1:
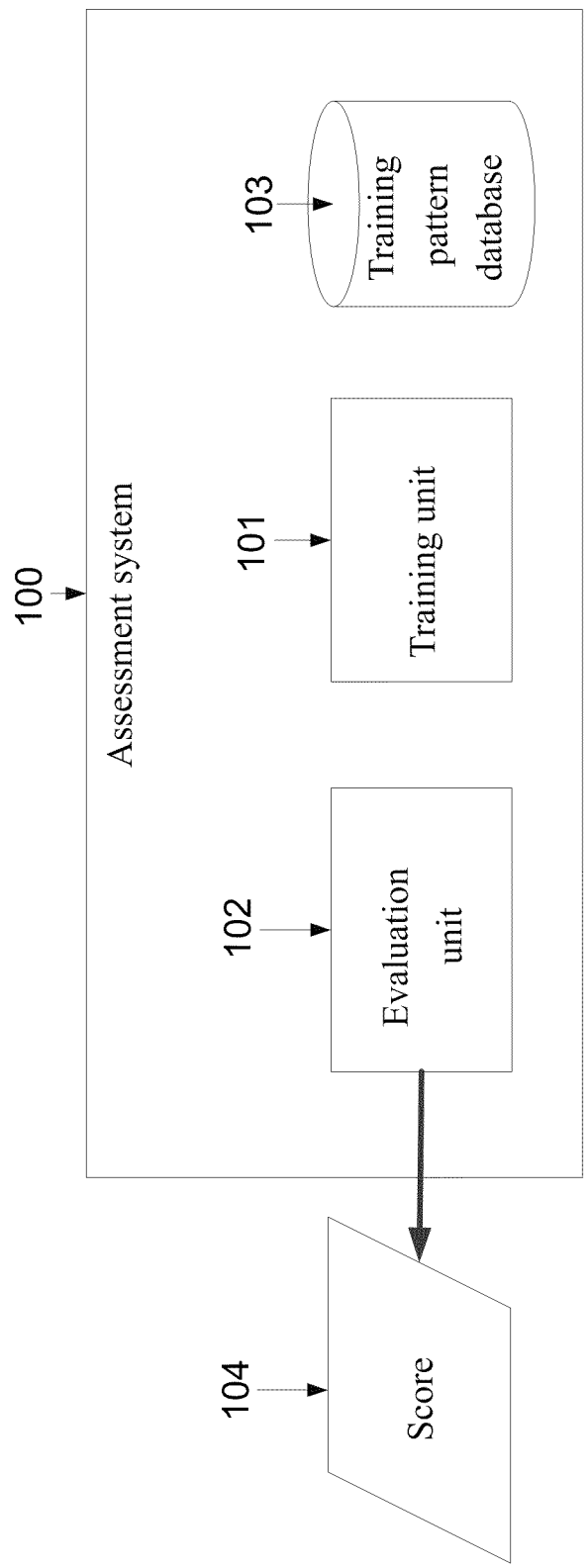

Reference is now made to FIG. 1, which is a schematic illustration of an assessment system 100 for evaluating one or more functional abilities of a patient, according to some embodiments of the present invention. As used herein, a functional ability means a neuromuscular ability and/or the ability to carry out a purposeful activity, to perform a function of the body, such as movement, sensation, and voiding, to operate one or more organs of the musculoskeletal system, and to use and/or control muscles and movements, which may be referred to herein as a motor-functional performance. The evaluation system may be used for diagnosing the rehabilitation process of a patient, monitoring the progress of a patient in a rehabilitation process, and/or adjusting rehabilitation exercises according to the level and/or the progress of the patient.

The assessment system 100 comprises and/or connected to a database 103 for storing one or more exercising patterns and a training unit 101, optionally adaptive, for exercising the patient according to the exercising patterns. The assessment system 100 further comprises an evaluation unit 102 for evaluating the functional performances of the patient that exercises using the training unit 101 and for evaluating the physical abilities of the patient according to the received functional performances. The evaluation unit 102 is designed to output the evaluation of the functional performances of the patient, optionally as a score.

In some embodiments of the present invention, the assessment system 100 is designed for evaluating the functional abilities of a patient that is in a physical rehabilitation, for example after an accident or a stroke. As used herein, rehabilitation means neuromuscular rehabilitation, occupational therapy, physical therapy, rehabilitation medicine exercises, or any other exercise that is designed to develop, maintain and restore movement and/or functional abilities of a patient.

The training unit 101 optionally includes is a robotic platform, such as the Reo™ Therapy System of Motorika™ Ltd. 523 Fellowship Road, Suite 228 Mount Laurel, N.J. 08054. Such a training unit is described in International patent Pub. No. WO2005/074373 published on Aug. 18 2005, in International patent Pub. No. WO2005/074371 published on Aug. 18 2005, and/or in International patent Pub. No. WO2005/074372 published on Aug. 18 2005, which are all incorporated herein by reference.

Optionally, the training unit 101 is adaptive, as further described below. The training unit 101 comprises one or more sensors for measuring the performances of the patient. For clarity, virtually any type of sensor, such as force, velocity, acceleration, Vision system, and/or position, is capable of use with the training unit 101, in various embodiments of the invention. In some embodiments of the invention, plurality of sensors are used to determine information regarding position or motion of at least a portion of the patient, such as the leg, the hand, and/or the arm. Optionally, the training unit 101 comprises one or more sensors, such as image sensors, for measuring the direction and/or amount of movement and/or speed of the leg, the hand, and/or the arm. Optionally, the training unit 101 comprises one or more physiological sensors, for example a muscle temperature sensor, such as skin surface sensor, are used to ensure, for instance as a safety feature, that the patient is sufficiently warmed up. Optionally, the at least one sensor is a force sensor. Optionally, the at least one sensor is a position sensor. Optionally, the at least one sensor is a velocity sensor. Optionally, the at least one sensor is an acceleration sensor.

Optionally, the training unit 101 comprises a force feedback module for applying force in one or more degrees of motion. In some embodiments, the applied forces act as a force field, optionally continuous, which impedes and/or guides a patient. Alternatively or additionally to spatial trajectories, orientation trajectories and/or speed trajectories are guided, supported and/or measured.

As described above, the database 103 is used for storing one or more exercising patterns. Optionally, the evaluation system comprises the database 103 or an interface that is used for accessing such a database. Optionally, the exercising pattern defines one or more exercises. In such an embodiment, the exercising pattern includes a set of one or more exercises. Each exercise defines one or more two-dimensional (2D) and/or three-dimensional (3D) trajectories, a resistance value, and/or an optimal performance time. Such an exercise may be a force exercise, a tempo exercise, and a proprioception. The exercise may define a set of points in 2D and/or 3D spaces. Optionally, the exercise defines a trajectory of an optimal limb manipulation. It should be noted that the training unit may also be adapted to exercise the patient according to cognitive exercises, such as memory training and crossword puzzles. In such an embodiment the cognitive exercise may yield a sub-score which is calculated as part of the functional evaluation score and/or as a separate rehabilitation score.

For example, FIGS. 2A-2G depicts schematic illustrations of exercises which are performed by an exemplary stick 302 that is part of an exemplary training unit 101, according to some embodiments of the present invention. Each one of FIGS. 2A-2G depicts a set of exemplary manipulations that comprises one or more trajectories. Each trajectory extends between two points in space, for example as shown at 303. For clarity, the exercise, which is depicted in FIG. 2A, may be referred to herein as a forwarded reach 3D exercise. The exercise that is depicted in FIG. 2B may be referred to herein as a forward thrust exercise. The exercise that is depicted in FIG. 2C may be referred to herein as an elbow ext-flex exercise. The exercise that is depicted in FIG. 2D may be referred to herein as a forward side reach 0 exercise. The exercise that is depicted in FIG. 2E may be referred to herein as a reach a cup to mouth exercise. The exercise that is depicted in FIG. 2F may be referred to herein as a forward side reach 25 exercise. The exercise that is depicted in FIG. 2G may be referred to herein as a Horizontal abduction exercise.

Optionally, the exercising pattern defines a set of one or more exercises, which are optionally ordered in an ascending level of difficulty. Each exercise is defined by a manipulation that includes a set of trajectories. For example, referral 311 shows an exercise that tests the ability of a patient to strait his upper limb in different angles.

In one embodiment of the present invention, the assessment system 100 performs a physical rehabilitation evaluation of an upper limb of the patient. In such an embodiment, the set of exercises defines a set of manipulations for the scapula, the shoulder, the elbow and/or the distal hand, for example the wrist and/or one or more of the fingers. Optionally, the exercising pattern defines an exercise that allows the evaluation of the quality of manipulation, the force the patient applies in different angles, the pinch and the grip parameters, a range of manipulation, and/or a manipulation magnitude.

As described above, the evaluation unit 102 measures the functional performances of a patient that is exercising using the training unit 101 and evaluates the function abilities thereof according to the received functional performances, in the light of the exercising pattern. Optionally, the evaluation unit 102 correlates the measured function abilities according to a manual rehabilitation evaluation scale, such as ARAT, SIS, MAS, FMA, WMFT, MFT, and MSS. Optionally, the evaluation unit 102 can be updated with any rehabilitation evaluation scale and/or with new scales which are defined by the operator of the system. As used herein, a visual rehabilitation evaluation scale means a quantitative evaluative instrument for allowing a clinician to perform a visual and/or a manual assessment of one or more functional abilities of a patient, a recovery of one or more functional abilities of a patient, and/or a progress of a patient in a process for recovering one or more functional abilities. The correlation with the visual rehabilitation evaluation scale allows the operator of the assessment system 100 to provide an objective evaluation of one or more functional abilities of the patient and/or to provide the progress of the patient in a rehabilitation plan. As used herein, an objective evaluation means an evaluation of patient performances, for example in a rehabilitation process, such as a physical rehabilitation process, that is performed in an automatic manner.

As commonly known, evaluating and/or re-evaluating a functional ability of a patient according to a visual rehabilitation evaluation scale is usually performed in a clinical center by a certified clinician. Such an evaluation and/or a re-evaluation requires from the patient to perform a set of exercises during about 40-50 minutes. Furthermore, the evaluation and/or the re-evaluation are usually set by a certified clinician that performs a visual assessment of kinematic parameters of the patient performance during the performance of the set of exercises. As most of the used manual rehabilitation evaluation scales are constructed from numerous steps, such evaluation is relatively time consuming and the effectiveness and/or the cost-effectiveness thereof depends on the clinician's capabilities. As further describe below, the assessment system 100 may perform a relatively high number of objective evaluations per hour. In such a manner, using the assessment system 100 may improve the profitability of different clinical centers by increasing the number of evaluations that clinical center performs.

In particular, SIS lasts about 45 minutes, FMA lasts about 30-45 minutes, MAS lasts about 30-40 minutes, WMFT lasts about 45 minutes, MSS lasts about 50 minutes, and MFT lasts about 30 minutes. It should be noted that each one of the aforementioned evaluations are performed by a certified clinician.

It should be noted that in some markets, for example in the US, the federal system of medical insurance for elderly (Medicare) and other systems of medical insurance finance outpatient physical therapy, such as rehabilitation, based on a list of fee schedules which is known as the current procedural terminology (CPT). The CPT includes therapy CPT codes which are based either on increments of 15 minutes or on the type of the provided service. The charge for a service-based code time independent and remain the same regardless to the time that it takes the clinician to provide the service. For example, a clinical center that provides a physical therapy evaluations, which are known as CPT 97001, charges the of medical insurance for a fix amount per evaluation, regardless to whether providing the evaluation took 15, 30, or 45 minutes. Other examples for service-based CPT codes are occupational therapy evaluation, which is known as CPT 97003, physical therapy re-evaluation, which is known as CPT 97002, and occupational therapy re-evaluation, which is known as CPT 97004. As the assessment system 100 scores the functional performances of a patient in less time than a certified clinician that performs a visual rehabilitation evaluation, the throughput of an operator that uses the assessment system 100 is higher than the throughput of a certified clinician that performs visual rehabilitation evaluations. Furthermore, the functional evaluation score and/or any of the sub-scores that have been calculated for providing can be used evaluating and/or predicting the performances of the patient in an exercise or a set of exercises, which are performed according to a visual rehabilitation evaluation scale, optionally as, outlined above and described below.

The assessment system 100 is designed to perform an evaluation by exercising the patient for about 15 minutes and to perform a re-evaluation by exercising the patient for about 5 minutes. The operating of the assessment system 100 does not require the presence of a certified clinician. Optionally, the operator of the assessment system 100 is a therapy aid personal, such as a technician. Optionally, the assessment system 100 comprises a control device, which is connected to a network, such as the internet, and includes a video camera. The control device optionally allows the operator to supervise on the evaluation or the re-evaluation from a remote location. Optionally, the control device includes a microphone a speakers and the operator can direct the exercising by instructing the patient from the remote location. Optionally, the control device can be connected to a remote terminal, such as a computer that is connected to the Internet. Such a control device allows the physician that has directed the patient to perform the evaluation and/or the re-evaluation to watch the patient and to be in touch with her during, before, and/or after the exercise from her office. Optionally, the assessment system 100 is positioned at the home of the patient, allowing her to perform the rehabilitations evaluations and/or re-evaluations in a familiar surrounding. In such an embodiment, the control unit allows the operator to direct the exercising of the user by instructing the patient from the remote location, optionally as described above.

As described above, the training unit 101 is designed to exercise the patient according to an exercising pattern that defines a set of one or more exercises. In an exemplary embodiment of the invention, the assessment system 100 includes a user interface that allows the operator of the assessment system 100 to select and/or to adjust the exercising pattern. Optionally, the user interface includes a keypad, a keyboard, and/or any other input unit that allows the user to input instructions and a display for feedback. Optionally, the user interface is a wired or wireless pendant or wrist-worn controller. Optionally, the user interface allows the operator to input medical information about the patient. As used herein, medical information means, inter alia, information which is related to the patient, such as laboratory results, therapeutic procedure records, clinical evaluations, age, gender, medical condition, ID, genetic information, patient medical record, data indicating of metabolism, blood pressure, patient history, sensitivities, allergies, different population records, treatment methods and the outcome thereof, epidemiologic classification, comorbidity, and patient history, such as treatment history. Optionally, the training unit 101 is designed to adjust and/or select the exercising pattern according to the inputted medical information, for example as described below. Optionally, the user interface allows the operator to add additional scores to the calculation of the functional evaluation score. Such additional scores may be based additional exercises and/or known rehabilitation accessories. Optionally, the user interface allows the operator to select an exercising pattern that is adjusted to the rehabilitation level of the patient and/or to his estimated functional abilities. In such an embodiment, the database 103 host a number of exercising patterns, each associated with a different level of functional ability.

Figure 3:
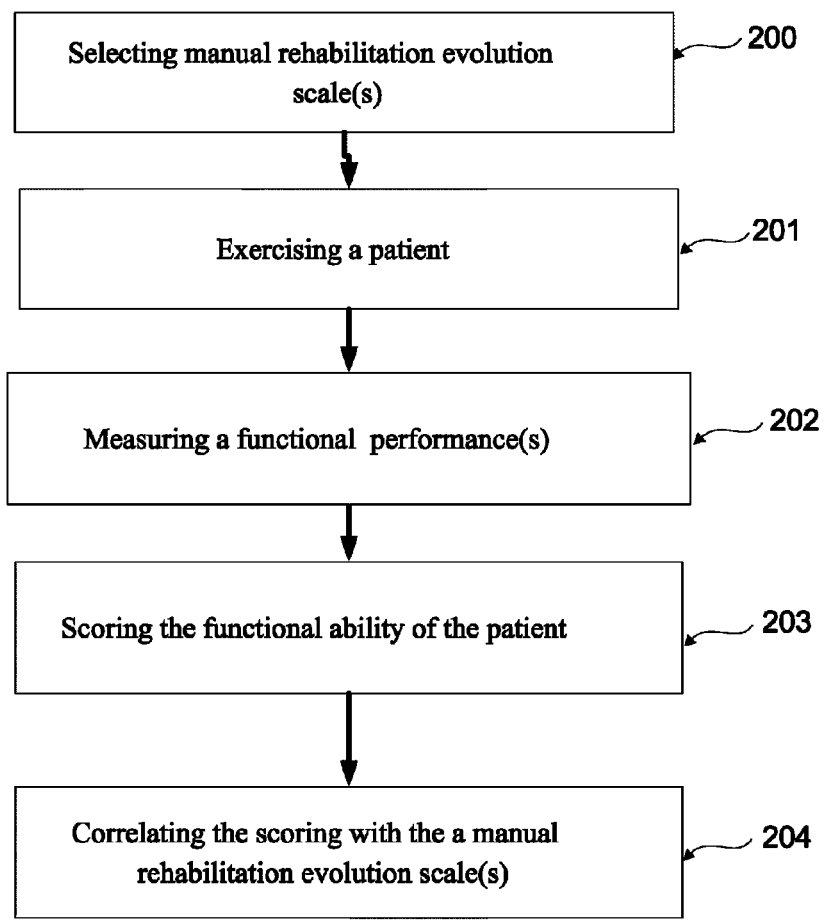

Reference is now also made to FIG. 3, which is a flowchart of a method for generating a performance score for a patient according to her functional performances. The method is described according to some embodiments of the present invention.

At first, as shown at 200, one or more manual rehabilitation evaluation scale, such as an action research arm test (ARAT), a stroke impact scale (SIS), Fugl-Meyer assessment (FMA), motor assessment scale (MAS), wolf motor function test (WMFT), motor status score for the Upper Extremity (MSS), manual function test (MFT), is selected. It should be noted that the step may also be performed later on, for example during the exercising of the patient. Optionally, the operator of the assessment system 100 uses the aforementioned user interface for selecting one or more manual rehabilitation evaluation scales from a list of manual rehabilitation evaluation scales.

Then, as shown at 201 and described above, the patient is exercised according to a predefined exercising pattern, using the training unit 101. Then, as shown at 202, the performances of the patient during the exercise are measured by the training unit 101. In some embodiments of the present invention, the training unit 101 measures two-dimensional and/or spatial manipulations of the patient, as described above. These manipulations are measured with respect to the time domain, allowing the evaluation of the functional performances of a patient with respect to the time of the performance of a manipulation and/or sub-manipulations takes. Optionally, the training unit 101 outputs and/or stores a record of the measured manipulations.

Then, as shown at 203, the physiological activity of the patient is scored, optionally by the evaluation unit 102, according to the measured functional performances in the light of the exercising pattern that has been used for exercising the patient. The evaluation unit 102 accesses and/or receives the measured functional performances. Then, the evaluation unit 102 processes and analyzes the measured functional performances and then generates one or more scores for the physical abilities of the patient. Optionally, the measured functional performances allow the scoring of the functional abilities of the patient according to a visual rehabilitation evaluation scale.

As shown at 204, the one or more scores are correlated with the selected one or more manual rehabilitation evaluation scale. Optionally, a functional evaluation score that evaluates the functional abilities of the patient is calculated according to a function, optionally weighted, that is based on one or more of the measured functional performances. Optionally, the functional evaluation score is determined according to sub-scores, such as one or more quality of movement scores and active or passive range of motion (ROM) scores. A quality of movement score may include a smoothness score, a path efficiency (PE) score, an active movement in motion direction score, which may be referred to herein as an active percentage, and a resistance to movement score. Active and passive ROM scores may include active efficiency (AE) score, muscle force (MF) score, an active ROM ratio score and/or a passive ROM ratio score.

As described above, the training unit 101 is designed to measure the performances of a patient. In order to evaluate these performances, the training unit 101 optionally guides a patient to perform a motion, which may be referred to herein as a manipulation, with a correct spatial trajectory, by applying one or more pushing, assisting, reminding, responding and/or resisting forces during a motion of the patient or an intent to move by the patient. Optionally, the training unit 101 provides feedback, optionally tactile, to the manipulations of the patient. Optionally, such feedback and/or guidance are provided mechanically by a rehabilitation robot, optionally the rehabilitation robot that is described in International patent Pub. No. WO2005/074371 published on Aug. 18 2005, which is incorporated herein by reference. Optionally, the training unit 101 comprises an actuator that applies feedback forces on a robotic articulated arm or a spherically jointed lever which is manipulated by the patient during the performance of the aforementioned set of exercises, for example as shown in FIGS. 2A-2G and/or described in International patent Pub. No. WO2005/074373 published on Aug. 18 2005, which is incorporated herein by reference.

Optionally, the training unit 101 supports, for a given volume of space and a given range of force strengths, substantially any 3D movement trajectory. The space that confines the movement trajectory may be referred to herein as an envelope of movement. Optionally, the envelope of movement supports a ROM of a healthy arm or a healthy leg in any dimension or volume. Optionally, the envelope of movement supports only a part of the range of motion, for example, 50% or 30% of such a volume.

Optionally, the training unit 101 is programmable with various exercising patterns; each comprises an exercise that is based on one or more trajectories that have various characteristics such as different paths, velocities, and/or forces. Optionally, the trajectory, which is defined in one or more of exercising patterns, is a dynamic trajectory. In such an embodiment, the trajectory may vary in response to the sensed path, velocity, and/or force of the patient's manipulations and/or in response to the progress of a patient during an exercise and/or during her progress in a rehabilitation plan. Optionally, the trajectories and/or the characteristics thereof are defined for one or more areas on same and/or different limb or body part.

The evaluation unit 102 is designed for analyzing the measured performances and to output a score based on the analysis. Optionally, the score is correlated with a manual rehabilitation evaluation scale, as described above. The score is calculated according to an analysis of different characteristics of the measured user performances. Optionally, the analysis is based on sub-scores that define a velocity profile, a difference between the exercising pattern and the one or more manipulations of the patient during the exercise, a stability of the manipulations trajectories, and/or a force the patient applies to the one or more manipulations. Optionally, the sub-scores are one or more of the following:

1. A smoothness sub-score—a sub-score that is determined according to the number of peaks in the velocity profile of one or more manipulations divided by the optimal number of peaks. For example, see FIG. 12 that is a graph depicting an ideal velocity profile of an estimated motion of a lever of a training unit, which is manipulated between two points by a healthy patient, and FIG. 13 that is a graph depicting an actual velocity profile for a motion of a lever of a training unit which is manipulated between two points during the performance of an exercise by an actual patient.
2. A PE sub-score—a sub-score that is determined according to the path length of the one or more measured manipulations divided by the distance between the played points through which are defined in the exercising pattern.
3. A resistance sub-score—a sub-score that is determined according to the percentage of time that the patient applied force, which is opposite, or substantially opposite to the trajectory that is defined in the exercises of the exercising pattern.
4. A synergic lift sub-score—a sub-score that is determined according to the maximum force, velocity, and/or path's length the patient has reached during the one or more manipulations of the exercise.

These sub-scores are optionally normalized to reflect value between 0 and 100, where o denotes no performance and 100 denotes full performance. In such an exercise, the patient is asked to lift a lever that is monitored by the training unit 101 from the lowest point in the sagittal plane up to the highest point.

5. An AE sub-score—a sub-score that is determined according to the percentage of time in which the patient has actively trained during the exercise. Optionally, the AE sub-score is determined according to the force and or path's length of the manipulations in the boundaries of the envelope of movement. For clarity, a passive envelope of movement defines the range of motion that is achieved by a patient's limb which is actuate by an active agent where the patient is totally passive and the agent is totally active. An active envelope of movement is the Range of motion that is achieved by the patient's limb without the assistance of any agent.
6. A fit free sub-score and/or an original sub-score—a sub-score that is determined according to the ratio between the area in which the manipulations have been measured, an area which may be referred to herein as an active envelope of movement, and the area that bounds the exercising pattern, an area which may be referred to herein as a passive envelope of movement.
7. A total path original (Cm) sub-score—a sub-score that is determined according to the distance between original exercise points and the measured manipulations.
8. A total path fit guided sub-score—sub-score that is determined after an evaluation is provided in a guided mode, according to a distance between the exercise points and the measured manipulations. The guided motion mode is substantially passive for the patient. The patient's hand is attached to a robot's guidance unit, such as a mast, and the training unit 101 moves the guidance unit between the exercise's points.
9. A total path fit free sub-score—sub-score that is determined after an evaluation in a free mode, according to a distance between the exercise points and the measured manipulations. The free motion mode is the active mode in which the manipulations of the patient are not supported by the training unit 101 and has to move a guidance unit between the exercise's points.
10. A fit guided sub-score and/or original sub-score—the percentage of a passive ability to an original envelope. Such sub-scores may also be documented in a non-specific flag. In such an embodiment, low value may indicate different problems, like short hands, pain, hyper or hippo tonicity, and/or fear of the system.

Optionally, the score 104 is given as a percentage of a reference value. Optionally, the reference value is a known norm value, a value representing the optimal capability of the patient, and a value representing previous scores of the patient, as further described below. The higher is the score; the better is the scored physical abilities of the patient.

In some embodiments of the present invention, the scores are acquired by measuring a set of exercises that examines manipulations of the user in a manner that allows correlating between the scores to scores which are given on a visual rehabilitation evaluation scale, such as ARAT, SIS, MAS, FMA, WMFT, MFT, and MSS. Optionally, a table of correlation values, for example as depicted in FIG. 7 and/or FIG. 8 and described in the experimental data which is described below, is used for correlating between the sub-scores and a score of a visual rehabilitation evaluation scale.

Figure 10A:
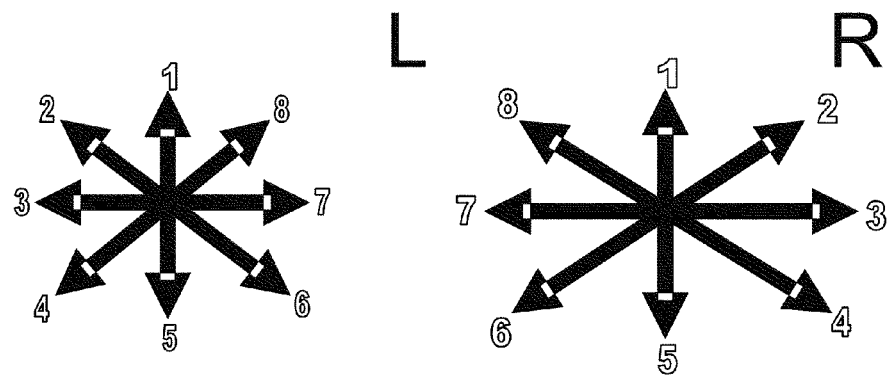
Figure 10B:
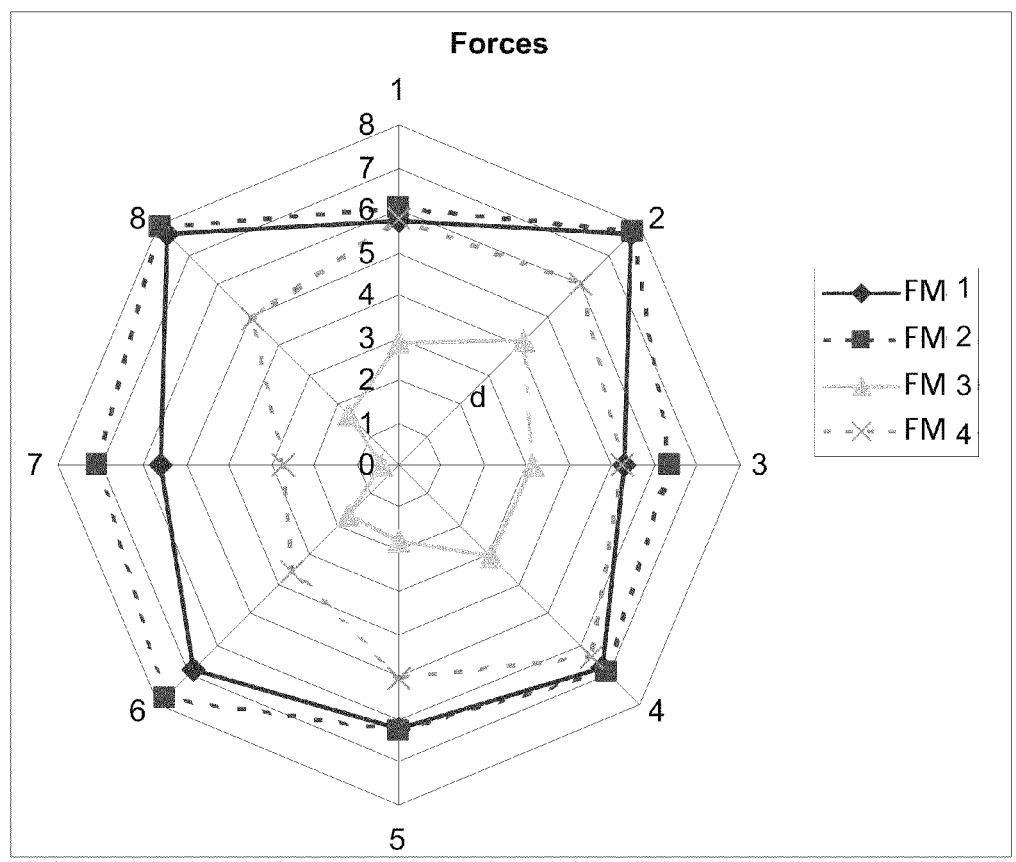

In some embodiments of the present invention, the assessment system 100 may be used for evaluating neuromuscular limitations which are caused by a loss of brain function, for example due to a brain stroke or any other interruption in the blood supply to all or part of the brain. Optionally, the assessment system 100 may be used for evaluating cognitive and/or speech abilities by exercising the patient according to exercises that indicates on the cognitive status of the patient, for example color matching, shapes matching, and math. The evaluation is based on normalized values, such as a normalized force and angle values which are measured according to the performance of the patient in a set of exercises. Optionally, the normalized force is a function that is based on a normal value and on the age and the sex of the patient. Optionally, respective normal values which are defined by the Occupational Safety & Health Administration (OSHA) or any other health organization. Optionally, the normal value, for example the normal value of the pinch and grip exercises, is defined as an outcome which given in the $95^{th}$ percentile of a plurality of measured values, for example the scores in the $95^{th}$ percentile of a plurality of patient that used the assessment system 100 for performing rehabilitation evaluations and/or re-evaluations It should be noted that a norm value may be a discrete value, for example as defined for pitch and grip exercises, and/or one or more vectors, for example as defined for force exercise in which the normal value is based on eight force measurements which are taken during the maneuvering of a lever along eight different directions. Each one of the scores which are used for calculating the norm value is calculated according to a ratio between the area of an octagon that is defined by lines that connect numbers representing the forces measured in each direction, for example as shown at FIG. 10B. The octagon is defined by the maximum forces that can be measured with the training unit 101.

Optionally, the angle values are normalized by calculating a ratio between the actual palmar flexion of the user and an optimal palmar flexion. As used herein, a palmar flexion means the bending level of the hand or fingers toward the palmar surface.

In such an embodiment, an exemplary exercising pattern that includes the following set of exercises is used:

1. Pinch—an exercise for evaluating the distal force of the fingers of the patient by measuring the normalized force that is applied by the patient.
2. Grip—an exercise for evaluating the distal functionality of the palm of the patient by measuring a normalized force that is applied by the patient.
3. Force-Star (F-star)—an exercise for evaluating the proximal functionality of the arm of the patient by measuring the normalized force that is applied by the patient. Optionally, the patient is instructed to use her arm for moving the aforementioned lever in a star shaped manipulation, for example as shown at FIG. 10A.
4. Wrist ROM (WROM)—an exercise for evaluating the distal functionality of the wrist of the patient by measuring the normalized angle of an arm movement of the patient. Optionally, the training unit 101 includes a rehabilitation device that guides a hand or arm of a patient through a series of movements, for example as described in International Patent Application No. IL2007/001239, filed on Oct. 16 2007, which is incorporated herein by reference. The distal functionality is evaluated using the rehabilitation device. As described in the International Patent Application No. IL2007/001239, the rehabilitation device is designed for logging various measurements which are made during the exercise. Such logging produces a feedback that reflects the physiological condition of the patient. For example, the rehabilitation device may evaluate the patient fatigue based on increased irregularities of motion and/or based on pulse rate or other physiological parameters. In such a manner, a Wrist ROM score may be evaluated.
5. Forward thrust (FT)—an exercise for evaluating proximal functionality by measuring the quality of movement and ROM of the patient's arm. Optionally, the exercise includes moving the aforementioned lever along a trajectory, for example as depicted in FIG. 2B. The training unit 101 calculates the PE, TE, and/or AE of the patient by logging and analyzing the displacement of the aforementioned lever along the trajectory.
6. Elbow extension/flexion (ELB)—an exercise for evaluating proximal functionality by measuring the quality of movement and ROM of the patient's arm. Optionally, the exercise includes moving the aforementioned lever along a trajectory, for example as depicted in FIG. 2C. The training unit 101 calculates the PE, TE, and/or AE of the patient by logging and analyzing the displacement of the aforementioned lever along the trajectory.
7. Reach waist level (RWL)—an exercise for evaluating proximal functionality by measuring the quality of movement and ROM of the patient's arm. Optionally, the exercise includes moving the aforementioned lever along a trajectory, for example as depicted in FIG. 2D. The training unit 101 calculates the PE, TE, and/or AE.
8. Reach shoulder level (RSL)—an exercise for evaluating proximal functionality by measuring the quality of movement and ROM of the patient's arm. Optionally, the exercise includes moving the aforementioned lever along a trajectory, for example as depicted in FIG. 2F. The training unit 101 calculates the PE, TE, and/or AE.
9. Horizontal abduction (HAB)—an exercise for evaluating proximal functionality by measuring the quality of movement and ROM of the patient's arm. Optionally, the exercise includes moving the aforementioned lever along a trajectory, for example as depicted in FIG. 2G. The training unit 101 calculates the PE, TE, and/or AE.

Optionally, the evaluation of one or more of the exercises includes the calculation of one or more of the following scores:

a PE score that is evaluated by calculating a ratio between an estimated path and an actual path of a limb during a certain manipulation;

a time efficiency (TE) score that is evaluated by calculating the ratio between an estimated and an actual time for manipulating a limb in a certain direction; and an AE score that is evaluated by calculating the ratio between an estimated and an actual ROM of a limb during a certain manipulation.

In such an embodiment, the training unit 101 measures the functional performances during the aforementioned exercises and optionally translates them to a vector of mathematical scores. These scores represent quality and quantity measurements of the movement.

Optionally, the set of exercises of the exercising pattern, for example as the aforementioned exemplary exercising pattern, is selected to yield scores which are substantially uncorrelated and linearly independent. In such an embodiment, each one of the exercises is performed to acquire a score that reflects one or more physical measurements which are not reflected by the scores of other exercises of the exercising pattern. In such a manner, an exercising pattern includes only exercises that yield scores which represent a unique combination of physical measurements. The unique combination of physical measurements provides additional information when it is used for orthogonal calculations. For example, a the outcome of a coordination exercise may be used for evaluating and/or re-evaluating scores and/or sub scores of a ROM exercise may be orthogonal to a time score in the same manner that a PE is }

Optionally, the scores are normalized. In such an embodiment, the scores are represented as a ratio, such as a percentage from a perfect score, optionally in the range between 0 and 100. Other scores, normalized to the 95 percentile are not bounded and in some instances, the score may exceed 100%.

Optionally, a functional evaluation score is calculated according to one or more of the scores of the exercises. The functional evaluation score and/or any of the exercise scores may be used for evaluating the rehabilitation of the patient. As used herein, a functional evaluation score means a score that defines the neuromuscular abilities of the patient and/or the ability to carry out a purposeful activity, to perform a function of the body, such as movement, sensation, and voiding, to operate one or more organs of the musculoskeletal system, and to use and/or control muscles and movements. Optionally, statistical and numerical methods are used for calculating the progress based on two or more separated outcomes of evaluations and/or re-evaluations of the patient. Such methods includes multiple regression analysis, factor analysis and cluster analysis.

Figure 4:
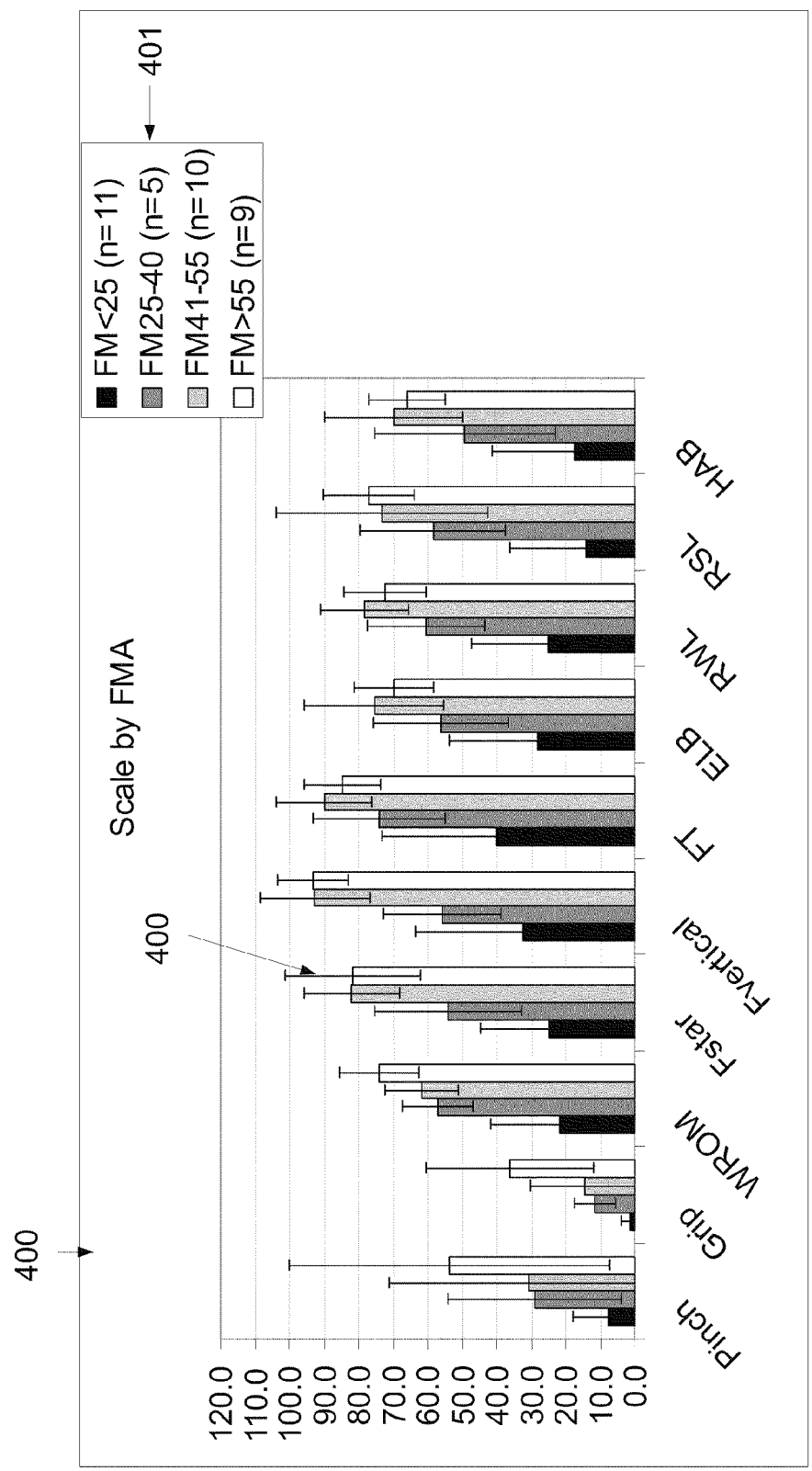

Reference is now also made to FIG. 4, which is a multiple column chart 400 that describes the distribution of scores of 35 experimental patients in the set of exercises of the exemplary exercising pattern that is provided above, according to some embodiments of the present invention. The chart 400 depicts scores, which have been given by the analysis unit 102 to a set of exercises that is measured by the training unit 101. The scores are given according to a scale that is based on the FMA. FIGS. 6-9 and the example that is provided below further describe the performances of the 35 experimental patients which are documented in FIG. 4.

Optionally, the training unit 101 is an adaptive training unit 101 that adjusts the exercising pattern according to a preliminary evaluation of the evaluation unit 102. Optionally, the exercising pattern is adjusted and/or selected from a database of exercising patterns according to the patient profile of the patient, which is optionally defined as described below, the rehabilitation history of the patient, and/or an initial evaluation. The preliminary evaluation allows the assessment system 100 to instruct the patient according to an exercising pattern that matches to her physical abilities and/or may score her physical abilities in a more accurate manner.

Figure 5:
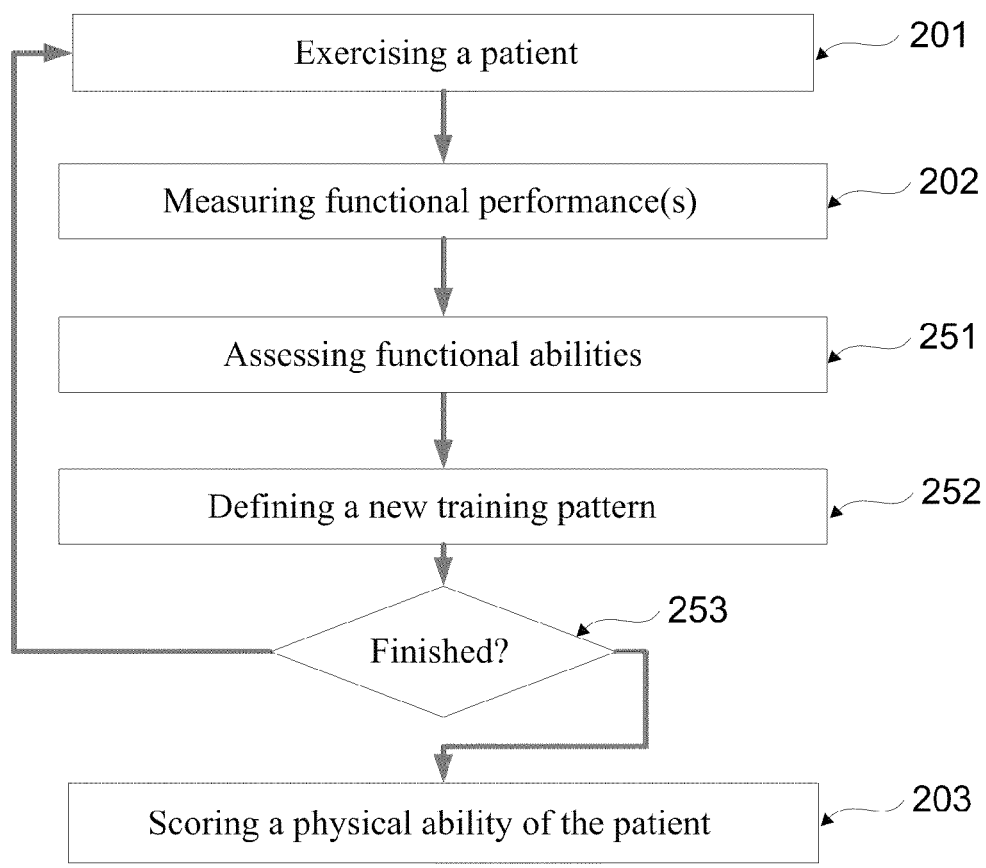

Reference is now made to FIG. 1 and to FIG. 5, which is a flowchart of a method for adaptive evaluation of a functional performance of a patient, according to some embodiments of the present invention. Blocks 201-203 are as depicted in FIG. 3. The addition of 251-253 depicts an iterative process that allows the adjustment of the exercises to the functional performances of the exercised patient. After the patient is exercised and one or more of her manipulations are measured, as shown at 201-202, one or more performance activities of the patient are assessed according to the measured manipulations, as shown at 251. Now, as shown at 252, the measurements allow defining a new exercising pattern according to the assessment. The new exercising pattern may include one or more functional exercises which are selected from a set of exercises which us stored in a database, for example as shown at 103. Optionally, the new exercising pattern is adjusted according to the manipulations, which have been measured, as shown at 202. Optionally, the new exercising pattern is outputted as a suggestion to the operator of the assessment system 100, for instance using the aforementioned user interface. The operator is optionally allowed to adjust the suggested exercising pattern and/or to change the one or more visual rehabilitation evaluation scales which may be used for correlating the measured functional abilities.

As shown at block 253, blocks 201, 202, and 251-252 are repeated with the new functional exercise that is defined in 252. The patient is exercised according to the new exercising pattern.

After the process ends, the physical ability of the patient is scored, as shown at 203 and described above. Optionally, the scoring is based on the last measurement or on a combination of some or all the measurements which have been assessed during the iterative process 253. Such an embodiment allows the assessment system 100 to define a new exercising pattern that is adjusted and/or selected dynamically according to an evaluation of the functional performances of the patient. For example, if the proximal functionality of the arm of the patient has been evaluated as low proximal functionality, for example as shown at the line FM-2 which is depicted in FIG. 10B, the new exercising pattern defines an exercise which is adjusted for a patent with low proximal functionality. Such an adjusted exercise allows exercising the patient with an exercising pattern that is adjusted according to her abilities and evaluating the proximal functionality of the patient within the range of low proximal functionality abilities. The adjusted exercising pattern may be defined to evaluate whether the proximal functionality abilities of the patient are on the underside, the top, or in any point on a scale that defines a range of low proximal functionalities. For example, the adjusted exercising pattern may guide the patient to follow a trajectory that is shorter and/or requires less force than the trajectory that is defined in a preliminary F-Star e Optionally, the assessment unit 100 is designed to adjust the scoring of the sub-scores and/or the functional evaluation scores to avoid inadequate level of precision of the score. Specifically, the evaluation unit 102 uses a measurement strategy that is utilized to avoid a lack of variability. In the case of a ceiling and/or floor effect, for example whenever the majority of sub-scores of patients in a certain exercise are at or near the maximum and/or minimum possible for the test, the scoring is adjusted according to sub-scores of one or more other exercises. For example, if the pattern of the sub-scores of a certain patient reflects that one or more of her sub-scores are at or around the minimum or the maximum of a related sub-score scale and that the percentage of the patients are located or around the minimum or the maximum of the related sub-score scale is high, for example as shown at 420 of FIG. 4, the weight which is given to these sub-scores is reduced in relation to one or more other sub-scores. Optionally, if such ceiling and/or floor effects are detected, a new exercising pattern, which is adjusted to exercise the patient in a manner that allows the evaluation thereof on a sub-scale, which is adjusted to his general functional abilities and/or reactions, is defined. The scoring of the performances of the patient on such a sub-scale allows the evaluation unit 102 to avoid the ceiling and or the floor effects.

Optionally, one or more preliminary exercising patterns are used for calibrating the assessment system 100 and the new exercising pattern are based on the calibration values. In such an embodiment, the calibration allows the generation of new exercising patterns, which are adjusted according to the functional abilities and/or reactions to the training unit 102, such as fear. Optionally, the calibration is based data from multiple patients that has been accumulated from a number of evaluation systems which are connected online. In addition, as the measured data is accumulated from various population segments, for example population segments which are divided according to comorbidities, age, and the like, the calibration, the score, and/or the sub-scores, may be compared in relation to the a related population segment.

In one embodiment of the present invention, the functional performances of the patient are stored and used for preparing a new exercising pattern. In such a manner, the assessment system 100 may be used for creating a dynamic rehabilitation program that is adjusted according to the progress of the patient. In such an embodiment, the user is exercised 201 according to the functional performances, which have been measured during his previous exercises, and/or the scores and/or functional evaluation scores she received for the previous exercises. Optionally, assessment system 100 is designed to exercise the patient in a number of sessions. During each session, which is not the first session, the exercising pattern of the training unit 101 is adjusted according to the scores and/or the functional performances, which have been given or measured during one or more previous sessions. For instance, if during a certain rehabilitation session, the assessment system 100 evaluates the functional performances of the patient to be in the 80 percentile of the related population, during the following session the assessment system 100 adjusts the exercising pattern to the 80 percentile. The adjustment may be performed by changing one or more of the trajectories of the exercises, the force that is applied on the limb of the patient during the exercise, and/or the resistance of the element that is guided by the patient.

For instance, when the used scale is based on FMA, each one of the set of exercises is selected according to a preliminary evaluation from four different tests. If the score of the patient in the preliminary evaluation is below 25, an exercise for low functional performances is applied. If the score is between 25 and 40, an exercise for medium functional performances is applied. If the score is between 41 and 55, an exercise for high functional performances is applied. If the score higher than 55, an exercise for very high functional performances is applied. For example, a patient with an FMA of 30 in the preliminary evaluation of a pitch exercise and 70 in the preliminary evaluation of a FT exercise is tested with a medium functional performances pitch exercise and high functional performances FT exercise.

It should be noted that the evaluation unit 102 may be designed for analyzing the measured manipulations of the patients and to output a functional evaluation score that may be correlated with other manual rehabilitation evaluation scales, such as ARAT, SIS, MAS, FMA, WMFT, MFT, and MSS, optionally as described above.

Optionally, the functional evaluation score is correlated with the ARAT scale, for example with the ARAT scale that is defined in one or more of Carroll D. "A quantitative test of upper extremity function" *J Chronic Diseases.* 1965; 18:479-491; Crow J L, Lincoln N N B, Nouri F M, De Weerdt W. "The effectiveness of EMG biofeedback in the treatment of arm function after stroke; *International Disability Studies,* 1989; 11:155-160. De Weerdt W J G, Harrison M A. "Measuring recovery of arm-hand function in stroke patients: a comparison of the Brunnstrom-Fugl-Meyer test and the Action Research Arm test, *Physiotherapy Canada.* 1985; and 37:65-70; Lyle R C "A performance test for assessment of upper limb function in physical rehabilitation treatment and research" *Int J Rehabil Res.* 1981;4: 483-492, which are incorporated herein by reference.

Usually, when an ARAT is performed, four abilities are evaluated: the ability to grasp an object, the ability to grip an object, the ability to pinch, and the ability to make gross movements. As used herein a GM means a relatively big body movement relating to the use of one or more large muscles of the body, such as those in the legs, the arms, and the abdomen. The set of exercise of the exercising pattern, which is designed to evaluate the ARAT score of the patient, comprises a set of manipulations that allows the evaluation unit 102 to evaluate the aforementioned four abilities.

Optionally, the sub-scores and/or the functional evaluation score are calculated with respect to the patient profile of the patient. In such an embodiment, the scores are optionally weighted and/or calculated differently according to different parameters of the patient profile. Optionally, the patient profile includes medical information about the patient.

It should be noted that the weighting of the medical information may assist in providing a score that reflects the progress of the rehabilitation process with respect to the medical condition of the patient. For instance, the existence of diseases or medical conditions of the patient, for example in the case of comorbidity, may have substantial effect on her functional performances. Optionally, if the rehabilitation process is related to a brain stroke, the score is adjusted according to the type and/or the location thereof.

Optionally, the sub-scores and/or the functional evaluation score are recorded. Optionally, the assessment system 100 is connected to an output unit, such as a screen and/or a printer, which allows the displaying of the scores in a functionality norm, such as low, medium, high and normal scores. Optionally, the output unit outputs and/or presents a report that includes graphical presentations of the scores and/or a profile of the patient that is based on her scores on the various exercises. Optionally, the profile may be used for diagnosing anatomical and functional limitations of the patient. Optionally, the profile may be used for evaluating the quality and/or the quantity of the movements of the patient. Such an output unit allows the generation of a report that describes and/or depicts the progress of the patient's performances based on previous exercises and/or scores. Such a report may be used for showing whether the functional abilities of the patient have been improved, unimproved, restored, worsened, and/or maintained. Optionally, the report depicts and/or described the scores and/or sub-scores of the patient in relation to a scale or a list of scores. Optionally, the report compares between the performances and/or the progress of the patient and related norm values. Optionally, the related norm values are dynamic. In such an embodiment, the related norm values are based on patient related information, such as the performances and/or the progress of various patients, which have been evaluated using the evolution system 100 or similar evolution systems. In such an embodiment, the evolution system 100 is optionally connected via a network, such as the Internet, to a central server that hosts scores, sub-scores, and/or exercise information of patients that used the evolution system 100 or similar evolution systems for evaluation and or re-evaluation, optionally as described above. Optionally, the evolution system 100 is part of a distributed system that includes a number of evolution systems and a central server for hosting the aforementioned scores, sub-scores, and/or exercise information. Optionally, the output unit comprises a classification unit that is designed to classify the performances and/or the progress of the patient according to predefined values or prototypes and/or using the aforementioned database. Optionally, the classification can be used for outputting a treatment recommendation or for adjusting the prospective rehabilitation exercises, evaluations, and/or re-evaluations. Optionally, the classification can be used for alerting the clinician and/or the patient whenever the score and/or one of the sub-scores are defined below and/or above a certain threshold. The alert may be visual, audible, and or tactile. Optionally, an alert is automatically sent, for example via the aforementioned control unit, to the physician that is in charged on the patient.

Various embodiments and aspects of the present invention as delineated hereinabove and as claimed in the claims section below find experimental support in the following experimental data, which together with the above descriptions, illustrates some embodiments of the invention in a non-limiting fashion. The experimental data is based on a trial that includes 53 patients. The experimental data is summarized in FIG. 6, which is a table that includes the measurements of 53 selected patients. The measurements where taken using the training unit which is described above.

In particular, the table includes the scores of 53 selected patients in a number of assessments that include FM proximal (FM_P) assessment, FM distal (FM_D) assessment, ARAT assessment, Wolf time (WT) assessment of a wolf motor function test (WMFT), Wolf weight (WW) assessment of a WMFT, and Motricity index. The table further includes a number of measurements which have been taken using the training unit. For clarity, the WT assessment represents the mean time required to perform functional tasks, optionally 14, with the paretic arm and hand. Maximum Wolf time is 120 seconds; moderate and severe impairment results in times above 80 and 120 seconds, respectively. The WW assessment represents a functional strength as the weight that the paretic arm may lift. Moderate and severe impairment correspond to 1 to 2 and 0 kg, respectively.

The experimental data, which is summarized in FIG. 6, allows the identification a set of correlation values, for example as depicted in FIG. 7, which is a table that comprises correlation values, each allows the conversion of one or more of the measurements, which are taken by the system or a combination of one or more thereof, to a sub-score of a visual rehabilitation evaluation scale, such as FM_P, FM_D, ARAT, WT, and WW. For example, the correlation value, which is shown at 370, allows the conversion of the F-star measurement to a respective ARAT sub-score.

Optionally, the correlation values are reduced to lower dimensions before they are used for correlating the measurements which are taken by the system. For example, FIG. 8 depicts a set of reduced correlation values that is based on a linear regression of the values of the table that is depicted in FIG. 7. For clarity, any other technique for reducing multidimensional data sets to lower dimensions for analysis may be used, for example principal components analysis (PCA). Optionally, the correlation values are reduced using the optimum transform in least square terms. It should be noted that due to the existence of a high degree of linear correlation among the correlation values, a backward stepwise procedure may be applied to obtain the reduced correlation values.

The reduced correlation values allow the calculation of expected scores for the patient. For instance, the expected FMA scores are matched with actual FMA scores, as shown at FIG. 11A, which is a chart depicting the expected FMA scores around a regression line that is based on the actual FMA scores. The expected WMFT scores are matched with actual WMFT scores, as shown at FIG. 11B, which is a chart depicting the expected WMFT scores around a regression line that is based on the actual WMFT scores. As depicted in FIGS. 11A and 11B, the regression line, which is based on the FMA scores or the WMFT scores, approximates the estimated FMA scores or the WMFT scores at a high rate. This may also be deduced from the high value of the coefficient of determination $R^2$ that reflects the proportion of variability of the scores. It should be noted that the scores, which are depicted in FIGS. 11A and 11B, have been acquired from two groups of patients having different functional abilities.

Furthermore, the data that is summarized in FIG. 6 may be used to identify correlation between various measurements, for example as depicted in FIG. 9, which is a table that depicts a set of intra-correlation values.

In some embodiments of the present invention, a set of exercises that is defined according to predefined clinician requirements is selected. Optionally, the set of exercises is set in a manner that a relatively high degree of lack of correlation exists among the functional abilities that each one of them evaluates. As used herein, predefined clinician requirements means a number of functional abilities that have to be evaluated in order to provide a certain score. Optionally, the predefined clinician requirements define a level of certainty for each one of the functional abilities. Optionally, the level of certainty is determined according to the medical condition of the patient. For example, the evaluation of functional abilities of a patient that is going through a complex rehabilitation process that may require a high level of certainty and the evaluation of functional abilities of a patient that is going through a regular rehabilitation process or a re-evaluation of functional abilities may require a low level of certainty. Optionally, the predefined clinician requirements define a set of constraints and the set of exercises includes the minimum number of exercises that fulfills set of constraints. Optionally, a minimum number of exercises are selected according to a relatively high degree of lack of correlation among the functional abilities which are evaluated according to the set of exercises, optionally as described below. In such a manner, the set of exercises may take less time than a set of exercises that includes a number of exercises that may be used for evaluating similar functional abilities.

Optionally, the intra-correlation values minimize the set of exercises of an exercising pattern. A first exercise that has a score with a high intra-correlation value with respect to a score of a second exercise, for example as shown at 372, may be used for estimating the score of the second exercise. For example, a regression function may be used for extracting scores for each one of the set of exercises and allowing the calculation of an estimation based thereupon.

The intra-correlation values minimization of the set of exercises of an exercising pattern. A first exercise that has a score with a high intra-correlation value with respect to a score of a second exercise, for example as shown at 372, may be used for estimating the score of the second exercise. For example, a regression function may be used for extracting scores for each one of the set of exercises and allowing the calculation of an estimation based thereupon.

As described above, the functional evaluation score may be calculated according to a number sub-scores which are calculated according to the performance of the patient in a number of respective exercises. Optionally, the training pattern comprises a minimized set of exercises that includes a minimum number of the exercises that is minimized to the extent possible within a set of requirement constraints. Optionally the set of requirement constraints includes a number of sub-scores that rank certain functional abilities. Optionally the set of requirement constraints is defined by a certain health authority a team or clinicians, and/or a medical publication. Optionally the exercises of the minimized set are selected in a manner that they have the lowest intra-correlation values. In such a manner, each required functional ability is scored by the lowest number of exercises and exercises with intra-correlation values between them are preferably not selected. Optionally, an intra-correlation table, such as the table that is depicted in FIG. 9, is used for selecting the exercises in the minimized set.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is expected that during the life of a patent maturing from this application many relevant systems, apparatuses, and methods will be developed and the scope of the term training units, sensors, and processors are intended to include all such new technologies a priori.

The terms "comprises", "comprising", "includes", "including", "having" and their conjugates mean "including but not limited to". This term encompasses the terms "consisting of" and "consisting essentially of".

As used herein, the singular form "a", "an" and "the" include plural references unless the context clearly dictates otherwise.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A computer-implemented method for computerized scoring at least one functional ability of a patient, comprising:
   using at least one computing unit, said computing unit including at least one processor in communication with at least one sensor located on a robotic rehabilitation platform, and with a non-transitory computer readable medium storing program code for implementation by said at least one processor, to perform the following:
   a) receiving an output of said at least one sensor configured for measuring an applied force applied by a patient exercising on said robotic rehabilitation platform configured to be manipulated by said patient by moving a mechanism module of said robotic rehabilitation platform according to a predefined exercising pattern defining a trajectory of a limb manipulation, wherein said trajectory extends between at least two points in a space;
   b) identifying at least one manipulation of at least one limb of said patient during said predefined exercising pattern by analyzing said received output of said at least one sensor;
   c) computing a functional evaluation score for said at least one functional ability according to said at least one identified manipulation, said functional evaluation score computed according to a function based on a plurality of sub-scores including at least one sub-score calculated from said measured applied force, each sub-score defining a functional component of said at least one manipulation of said at least one limb during said at least one trajectory performed by said patient compared to a full performance capability reference value, and said at least one sub-score includes at least one member selected from the group consisting of: a quality of movement score, an active range of motion score, and passive range of motion score; and
   d) converting said computed functional evaluation score to a respective score of a manual rehabilitation evaluation scale using at least one correlation value obtained from a database storing correlation values between functional ability scores and said manual rehabilitation evaluation scale, to generate an objective evaluation of said patient based on said manual rehabilitation evaluation scale;
   wherein said manual rehabilitation evaluation scale comprises a member selected from a group consisting of: an action research arm test (ARAT), a stroke impact scale (SIS), a motor assessment scale (MAS), a wolf motor function test (WMFT), a motor status score for the Upper Extremity (MSS), and a manual function test (MFT).

2. The method of claim 1, further comprising generating a single functional evaluation score according to said plurality of sub-scores.

3. The method of claim 1, further comprising diagnosing said patient with regard to said functional ability according to said manual rehabilitation evaluation scale.

4. The method of claim 1, further comprising using said manual rehabilitation evaluation scale for monitoring a therapy given to said patient with regard to said functional ability.

5. The method of claim 2, wherein said functional evaluation score is a neuromuscular evaluation.

6. The method of claim 1, wherein said computing said functional evaluation score comprises giving a rehabilitation score to said functional ability, said exercising pattern comprising a plurality of rehabilitation exercises.

7. The method of claim 1, wherein said exercising pattern define a member selected from a group consisting of: a Pinch exercise, a Grip exercise, a force-star (F-Star) exercise, a wrist range of motion (WROM) exercise, a forward thrust (FT) exercise, an elbow extension/flexion (ELB) exercise, a reach waist level (RWL) exercise, a reach shoulder level (RSL) exercise, and a horizontal abduction (HAB) exercise.

8. The method of claim 1, wherein said at least one manipulation comprises a three dimensional (3D) manipulation.

9. The method of claim 1, further comprising repeating a) and b) after said c) with an adjusted exercising pattern and adjusting said functional evaluation score according to said at least one manipulation performed of said repeated b), said exercising pattern being adjusted according to said functional evaluation score.

10. The method of claim 9, wherein said adjusted exercising pattern comprises at least one rehabilitation evaluation exercise for evaluating the progress of said patient with regard to said functional ability.

11. The method of claim 10, wherein said at least one rehabilitation evaluation exercise for evaluating the progress of said patient with regard to said functional ability comprises evaluating a rehabilitation re-evaluation score according to said at least one sensed manipulation.

12. The method of claim 10, wherein said at least one rehabilitation evaluation exercise for evaluating the progress of said patient with regard to said functional ability comprises evaluating a progress of said patient according to said at least one sensed manipulation.

13. The method of claim 9, wherein said adjusting allows the overcoming of at least one of a ceiling effect and a floor effect.

14. The method of claim 9, wherein said at least one functional ability comprises a plurality of abilities, said exercising pattern being adjusted according to scoring at least some of said plurality of abilities according to the score of at least one of the others of said plurality of abilities.

15. The method of claim 1, wherein said functional evaluation score is computed according to medical information pertaining to the patient.

16. The method of claim 15, wherein said medical information is selected from a member of a group consisting of: a laboratory result, a therapeutic procedure record, a clinical evaluation, age, gender, a medical condition, genetic information, a patient medical record, a metabolism related data, a blood pressure, a sensitivity, an allergy, a population relevance, a treatment, a treatment outcome, an epidemiologic classification, comorbidity, a treatment history.

17. The method of claim 1, wherein at least one of said scored functional ability is scored with a member selected from a group consisting of: a quality of movement score, active range of motion (ROM) score, resistance score, passive ROM score, a smoothness score, a path efficiency score, a motion direction score, and a resistance to movement score.

18. The method of claim 1, wherein said exercising pattern comprises a member selected from a group consisting of: applying forces, pushing forces, assisting forces, reminding forces, responding forces, and resisting forces during said at least one manipulation.

19. The method of claim 2, wherein said generating comprises calculating said functional evaluation score according to medical information pertaining to the patient.

20. The method of claim 1, wherein said exercising pattern comprises adjusting said exercising pattern according to said at least one manipulation during said identifying.

21. The method of claim 20, wherein said adjusting is performed according to a member selected from a group consisting of: the path of said at least one sensed manipulation, the velocity of said at least one sensed manipulation, the force of said at least one sensed manipulation, a compression to at least one previously sensed performance activity.

22. The method of claim 2, further comprising evaluating physiological limitations of the patient according to said functional evaluation score.

23. The method of claim 22, wherein said physiological limitations comprise a limitation selected from a group comprising: a motor limitation, a cognitive limitation and/or a speech limitation.

24. A system for scoring at least one functional ability of a patient, comprising:
a database configured for hosting at least one predefined exercising pattern, wherein each exercise pattern defines a trajectory of a limb manipulation, wherein said trajectory extends between at least two points in a space, and for storing correlation values between functional ability scores and at least one manual rehabilitation evaluation scale;
at least one sensor configured for measuring an applied force by a patient moving a mechanism module of a robotic rehabilitation platform configured to be manipulated by said patient, said at least one sensor located on said robotic rehabilitation platform, said at least one sensor configured for sensing at least one manipulation of at least one limb of said patient exercising according to at least one predefined exercising pattern; and
at least one computing unit including at least one processor in communication with said at least one sensor, and with a non-transitory computer readable medium storing program code for implementation by said at least one processor, said code comprising:
instructions to compute a functional evaluation score for said at least one functional ability according to said at least one sensed manipulation, said functional evaluation score computed according to a function based on a plurality of sub-scores including at least one sub-score calculated from said measured applied force, each sub-score defining a functional component of said at least one manipulation of said at least one limb during said at least one trajectory of said at least one manipulation performed by said patient wherein each sub-score is compared to a full performance capability reference value, and said at least one sub-score includes at least one member selected from the group consisting of: a quality of movement score, an active range of motion score, and a passive range of motion score, and for converting said computed functional evaluation score to a respective score of said at least one manual rehabilitation evaluation scale, to generate an objective evaluation of said patient based on said manual rehabilitation evaluation scale;
wherein said manual rehabilitation evaluation scale comprises a member selected from a group consisting of: an action research arm test (ARAT), a stroke impact scale (SIS), a motor assessment scale (MAS), a wolf motor function test (WMFT), a motor status score for the Upper Extremity (MSS), and a manual function test (MFT).

25. The system according to claim 24, further comprising:
said database configured for hosting at least one preliminary exercising pattern and a plurality of adjusted exercising patterns; and
wherein said code further comprises:
instructions to provide a preliminary evaluation of the at least one functional ability according to at least one preliminary exercising pattern; and
instructions to select at least one of said plurality of adjusted exercising patterns according to said preliminary evaluation.

26. The system of claim 25, wherein said preliminary evaluation is a rehabilitation evaluation and each said adjusted exercising pattern being a rehabilitation re-evaluation exercise.

27. The system of claim 24, wherein said database is configured for hosting a plurality of manual rehabilitation evaluation scales, further comprising a user interface configured for allowing an operator of the system to select one of said plurality of manual rehabilitation evaluation scales, and further comprising instructions for scoring said exercising according to said selected manual rehabilitation evaluation scale.

28. The system of claim 24, wherein said code comprises instructions to measure time during said exercising, said functional evaluation score scoring being computed according to said measured time.

29. The method of claim 1, wherein said manual rehabilitation evaluation scale is a visual rehabilitation evaluation scale that is manually evaluated.

30. The method of claim 1, wherein said manual rehabilitation evaluation scale includes evaluation of legs.

31. The method of claim 1, wherein said converting said computed functional evaluation score to a respective score of a manual rehabilitation evaluation scale comprises correlating between sub-scores of said at least one functional ability and a score of said manual rehabilitation evaluation scale.

32. The method of claim 1, wherein said manual rehabilitation evaluation scale comprises at least one subjectively evaluated sub-score.

33. The method of claim 1, further comprising adjusting said exercise pattern based on said respective score based on said manual rehabilitation evaluation scale.

34. The method of claim 1, wherein a sub-score of said plurality of sub-scores comprises a member selected from a group consisting of: a velocity profile of the identified at least one manipulation, a difference between the predefined exercising pattern and the identified at least one manipulation, a stability of a trajectory of the identified at least one manipulation, and a force applied by the patient during the identified at least one manipulation.

35. The method of claim 1, wherein a sub-score of said plurality of sub-scores comprises a member selected from a group consisting of: a percentage of time in which the patient has actively trained during said exercising, and a ratio between an active envelope of movement in which the identified at least one manipulation has been measured and a passive envelope of movement that bounds the predefined exercising pattern.

36. The method of claim 1, wherein a sub-score of said plurality of sub-scores comprises a member selected from a group consisting of: a distance between predefined exercise points and the identified at least one manipulations during a guided mode, a distance between predefined exercise points and the identified at least one manipulations during a guided mode during a free mode, and a percentage of a passive ability to an original envelope.

37. The method of claim 1, wherein said mechanism module is a stick.

38. The method of claim 1, wherein said at least one limb of said patient comprises at least one of hand, arm, and leg.

39. The method of claim 1, wherein said mechanism module of said robotic rehabilitation platform comprises at least one of an articulated arm, and a spherically jointed lever.

* * * * *